United States Patent [19]

Sivakumar et al.

[11] Patent Number: 5,413,719
[45] Date of Patent: May 9, 1995

[54] FLUORESCENT TRACER IN A WATER TREATMENT PROCESS

[75] Inventors: Ananthasubra Sivakumar; Jitendra Shah; Narasimha M. Rao, all of Naperville; Scott S. Budd, Aurora, all of Ill.

[73] Assignee: Nalco Chemical Company, Naperville, Ill.

[21] Appl. No.: 182,927

[22] Filed: Jan. 18, 1994

[51] Int. Cl.⁶ .............................................. C02F 1/56
[52] U.S. Cl. ............................. 210/708; 210/709; 210/734; 210/735; 210/736; 210/745; 210/917; 210/928; 436/56
[58] Field of Search .............. 210/708, 709, 725, 727, 210/710, 728, 734, 735, 745, 917, 928, 736; 436/55, 56

[56] References Cited

U.S. PATENT DOCUMENTS

| | | | |
|---|---|---|---|
| 4,783,314 | 11/1988 | Hoots et al. | 210/696 |
| 5,128,419 | 7/1992 | Fong et al. | 521/351 |
| 5,171,450 | 12/1992 | Hoots | 210/701 |

*Primary Examiner*—Peter A. Hruskoci
*Attorney, Agent, or Firm*—James J. Drake; Robert A. Miller

[57] ABSTRACT

A method for optimizing the dosage of a polyelectrolyte treating agent in a water treatment process using a fluorescent material having the opposite electrical charge as a polyelectrolyte treating agent used to treat water in a water treatment process.

6 Claims, 32 Drawing Sheets

FLUORESCENT TRACER IN A WATER TREATMENT PROCESS

BACKGROUND OF THE INVENTION

Field of the Invention

The present invention is in the technical field of monitoring and controlling the dosage of cationically charged polymeric water treatment chemicals which are used in liquid/solids and liquid/liquid separation processes.

Description of the Prior Art

Cationically charged water soluble or water dispersible polymers are utilized in a variety of processes that involve the separation of solids or immiscible liquids dispersed or suspended in water from water, and the dewatering of solids containing water. These types of polymers, which may be natural or synthetic, are broadly termed coagulants and flocculants. These polymers can be utilized in such diverse processes as emulsion breaking, sludge dewatering, raw water clarification, drainage and retention aids in the manufacture of pulp and paper, flotation aids in mining processing and color removal.

Polymers of this type generally work by neutralizing the anionic charge of the suspended solids, or liquids, which are to be removed. These solids or liquids may be waste which must be removed from water, or desirable products which are recovered from aqueous systems, such as, coal fines, which can be coagulated or flocculated and sold as fuel.

In the water treatment field of solids/liquid separation, suspended solids are removed from water by a variety of processes, including sedimentation, straining, flotation, filtration, coagulation, flocculation, emulsion breaking and the like. Additionally, after suspended solids are removed from the water they must often be dewatered so that they may be further treated or properly disposed. Liquids treated for solids removal often have as little as several parts per billion of suspended solids or dispersed oils, or may contain large amounts of suspended solids or oils. Solids being dewatered may contain anywhere from 0.25 weight percent solids, to 40 or 50 weight percent solids material. Liquid/solids separation processes are designed to remove solids from water, or, liquids from solids.

While strictly mechanical means have been used to effect solids/liquid separation, modern methods often rely on mechanical separation techniques which are augmented by synthetic and natural cationic polymeric materials to accelerate the rate at which solids can be removed from water. These processes include the treatment of raw water with cationic coagulant polymers which settle suspended inorganic particulates and make the water usable for industrial or municipal purposes. Other examples of these processes include the removal of colored soluble species from paper mill effluent wastes, the use of organic flocculant polymers to flocculate industrial and municipal waste materials, a sludge recovery and emulsion breaking.

Regarding the mechanism of separation processes, particles in nature have either a cationic or anionic charge. Accordingly, these particles often are removed by a water soluble coagulant or flocculant polymer having a charge opposite to that of the particles. This is referred to as a polyelectrolyte enhanced liquid/solids separation process, wherein a water soluble or dispersible ionically charged polymer is added to neutralize the charged particles or emulsion droplets to be separated. The dosage of these polymers is critical to the performance of the process. Too little ionically charged polymer, and the suspended particles will not be charge neutralized and will thus still repel each other. Too much polymer, and the polymer will be wasted, or worse, present a problem in and of itself.

If the polyelectrolyte or ionically charged polymer being added is very effective for the given process, the polyelectrolyte that leaves with the water fraction generally represents an overdosage. More polyelectrolyte was added than required. If the polyelectrolyte being added is not very effective for the given process, significant amounts of polymer may leave the process with the water fraction as an indication of the polymer's performance deficiencies. In either instance, a determination of the amount of polyelectrolyte that leaves a separation process with the filtrate or water fraction would be extremely beneficial. An effective polyelectrolyte should be added to a separation process in an amount just at or above that consumed by attachment to the solid or oil surface. Whether the dosage selected approaches this optimal dosage could be determined, and the dosage adjusted if necessary, if the level of the polyelectrolyte in the filtrate could be easily monitored. A less effective polyelectrolyte could be readily detected, and the polyelectrolyte selection changed, if the level of the polyelectrolyte in the filtrate could be easily monitored.

Monitoring the concentration of polyelectrolyte in the filtrate is a formidable task not well suited to industrial applications. Analytical techniques such as colloid titration are complicated and time consuming and do not permit a real time result. Electronic instrumentation to determine charge is available, but such devices are expensive, and do not differentiate between charge associated with a polymer, or charge from other sources, including the water, solids, or other constituents in the effluent. Time consuming measurements are inefficient since the characteristics of a waste stream or emulsion may vary considerably with time.

The use of fluorescence emission spectroscopy to determine the concentration of a fluorescent chemical species is extremely rapid and sensitive, but the species being monitored must be fluorescent. A typical polyelectrolyte is not fluorescent or is not sufficiently fluorescent for monitoring by emission spectroscopy. Since the polyelectrolyte in its performance is consumed in the sense that it attaches to the solids and/or oils and is separated from the water therewith, adding a fluorescent signature chemical or tracer that follows the water would not reveal what fraction of the polyelectrolyte has been consumed, even if the concentration of the tracer can be correlated to polyelectrolyte dosage.

While determining polyelectrolyte dosage, for instance by adding a tracer in known proportion to the polyelectrolyte and monitoring the tracer concentration to determine if the target dosage or feed rate is being met, may in and of itself be of significant assistance, a water-soluble totally inert tracer is an indicator of only the theoretical zero-consumption concentration of the polyelectrolyte in the filtrate, and not the actual filtrate concentration of the polyelectrolyte. A signature chemical or tracer that itself preferentially follows the solids and/or oil likewise is not an indicator of polyelectrolyte consumption and hence polyelectrolyte performance.

It is therefore an object of this invention to provide a process for monitoring a polyelectrolyte water treatment chemical that is consumed in its performance, preferentially associating with one phase in a multiphase system.

It is an object of the present invention to monitor a polyelectrolyte that preferentially associates with one phase of a multiphase system by determining the extent of such preferential association.

It is an object of the present invention to determine the extent of preferential phase association of a polyelectrolyte in a multiphase system using a technique that is rapid and sensitive. It is an object of the present invention to determine the extent of preferential phase association of a polyelectrolyte in a multiphase system using a technique that can be employed on a semi-continuous or continuous basis.

It is an object of the present invention to determine the extent of preferential phase association of a polyelectrolyte in a multiphase system using a technique that can be employed on line. It is an object of the present invention to determine the extent of preferential phase association of a polyelectrolyte in a multiphase system using a technique that determines the concentration of the polyelectrolyte in the nonpreferred phase. These and other objects of the present invention are described in detail below.

SUMMARY OF THE INVENTION

One aspect of the invention provides a method for optimizing the dosage of a polyelectrolyte treating agent in a water treatment process. The method comprises the steps of adding a known amount of a polyelectrolyte treating agent to water being treated in a water treatment process. Then, a fluorescent material having the opposite electrical charge as the polyelectrolyte is added to the water treatment process in a concentration of from 0.001 to 750,000 parts per million based on the known amount of the polyelectrolyte being added to the process. The polyelectrolyte and fluorescent material forms a complex based on their opposite charges. The water treatment process is then conducted normally to obtain an aqueous effluent. The fluorescent material is then monitored in the aqueous effluent to adjust the dosage of the polyelectrolyte based upon the amount of charged fluorescent material in the aqueous effluent.

PREFERRED EMBODIMENTS OF THE INVENTION

Figure 1:
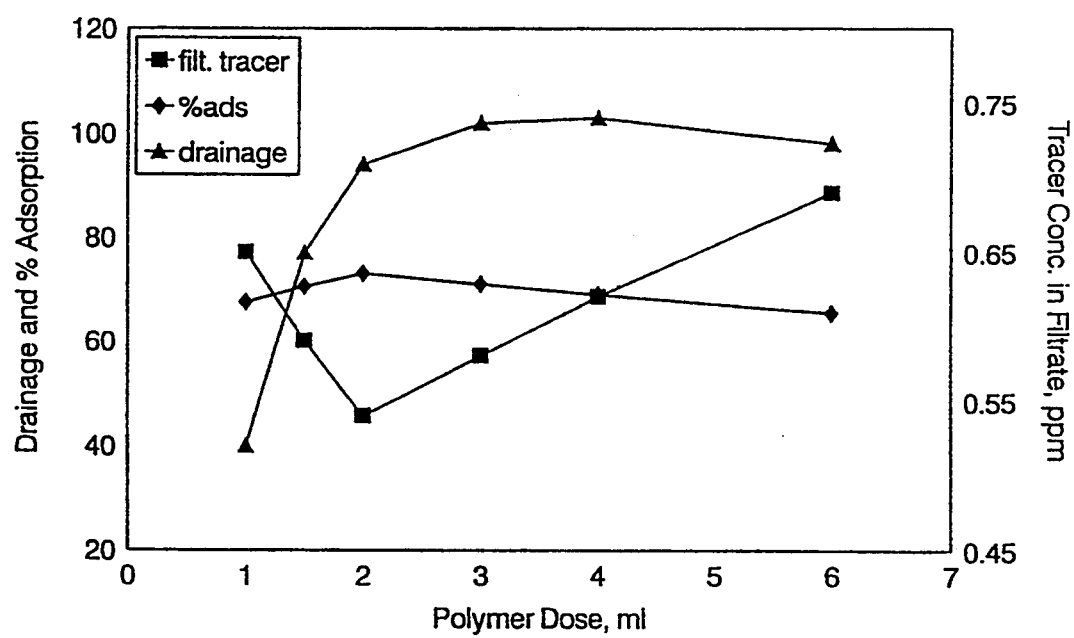
FIG. 1 is a graph comparing polymer dose to drainage and percentage adsorption for Polymer A.
Figure 2:
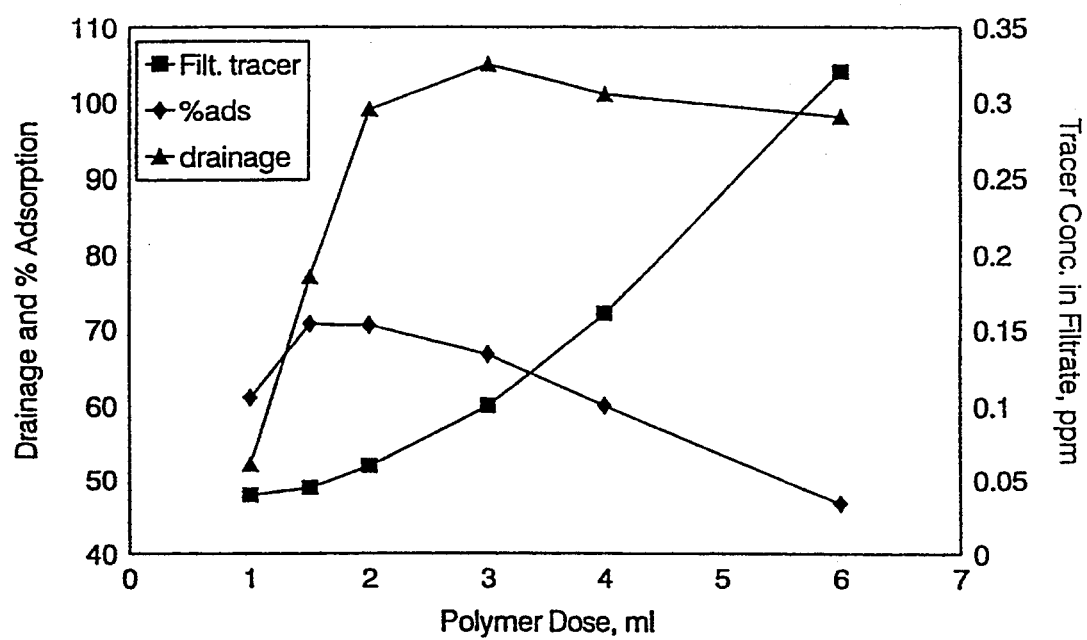
FIG. 2 is a graph comparing polymer dose to drainage and percentage adsorption for polymer A.
Figure 3:
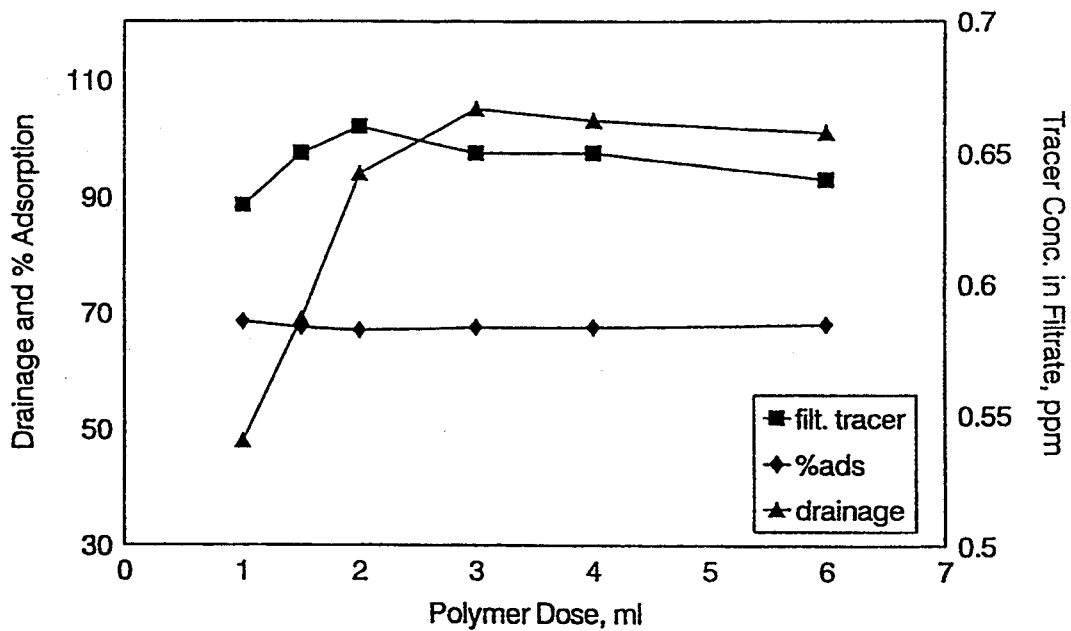
FIG. 3 is a graph comparing polymer dose to drainage and percentage adsorption for polymer A.
Figure 4:
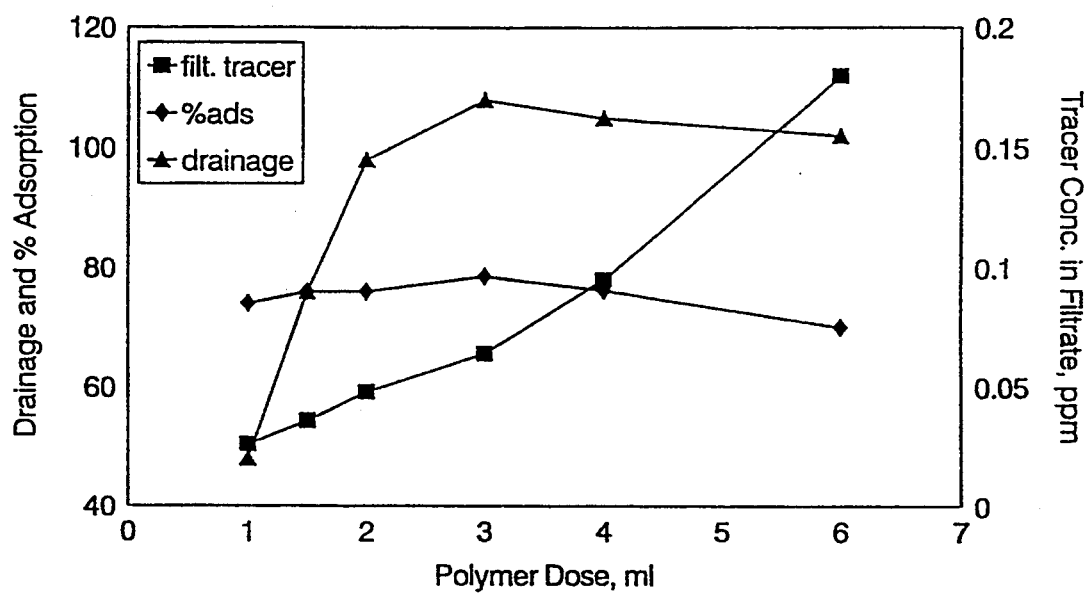
FIG. 4 is a graph comparing polymer dose to drainage and percentage adsorption for polymer A.
Figure 5:
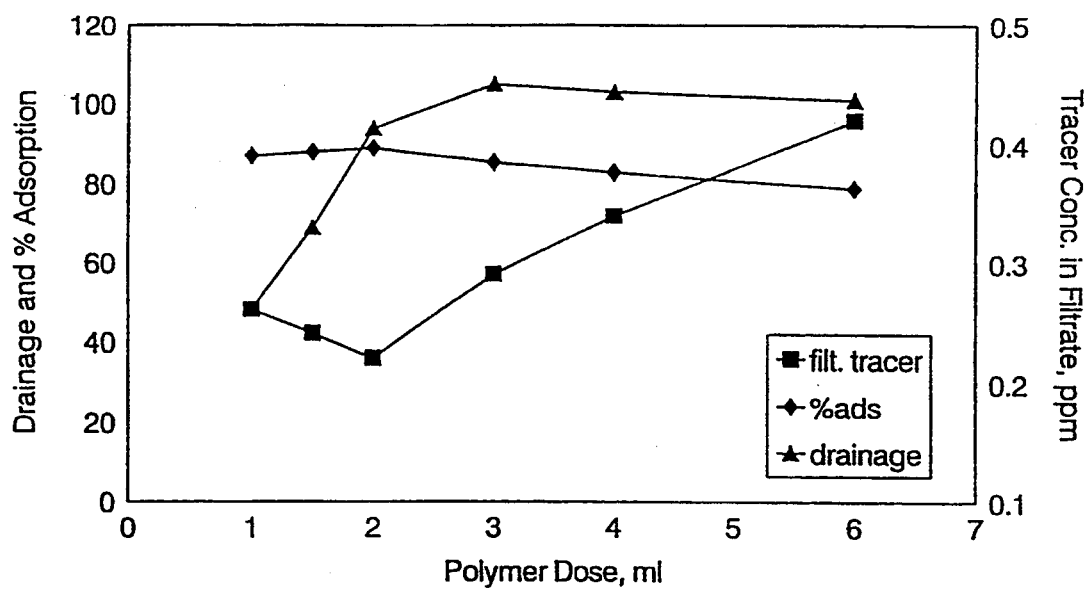
FIG. 5 is a graph comparing polymer dose to drainage and percentage adsorption for polymer A.
Figure 6:
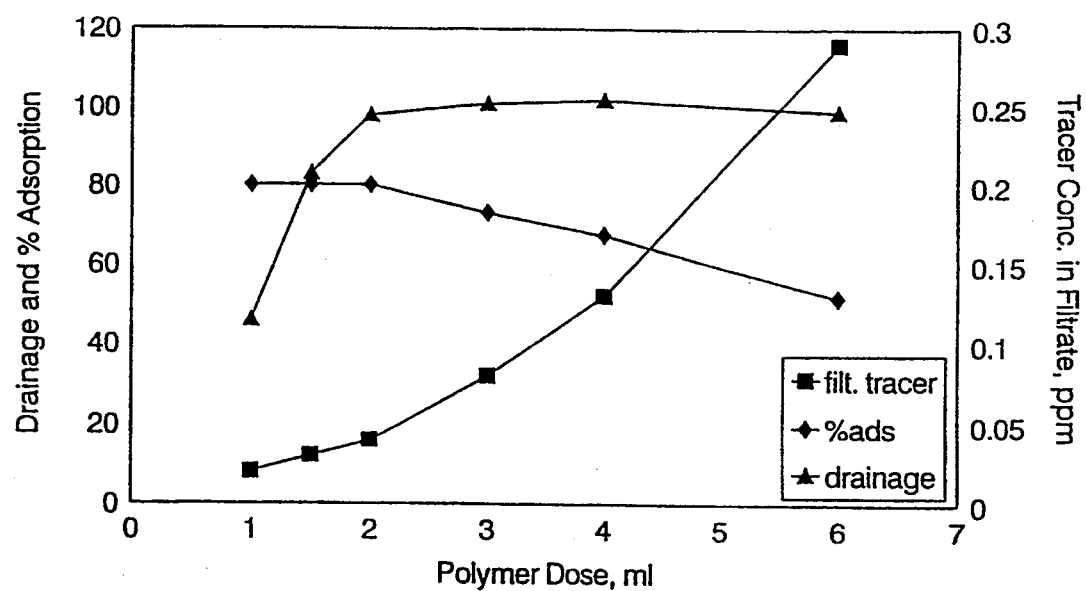
FIG. 6 is a graph comparing polymer dose to drainage and percentage adsorption for polymer A.
Figure 7:
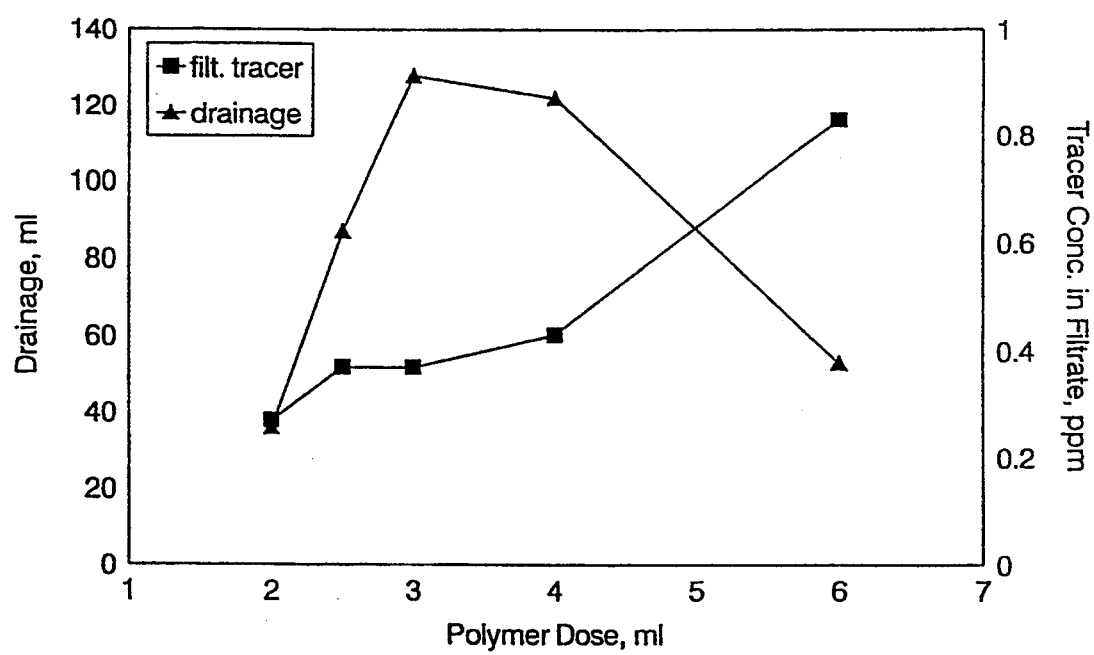
FIG. 7 is a graph comparing polymer dose to drainage and percentage adsorption for polymer B.
Figure 8:
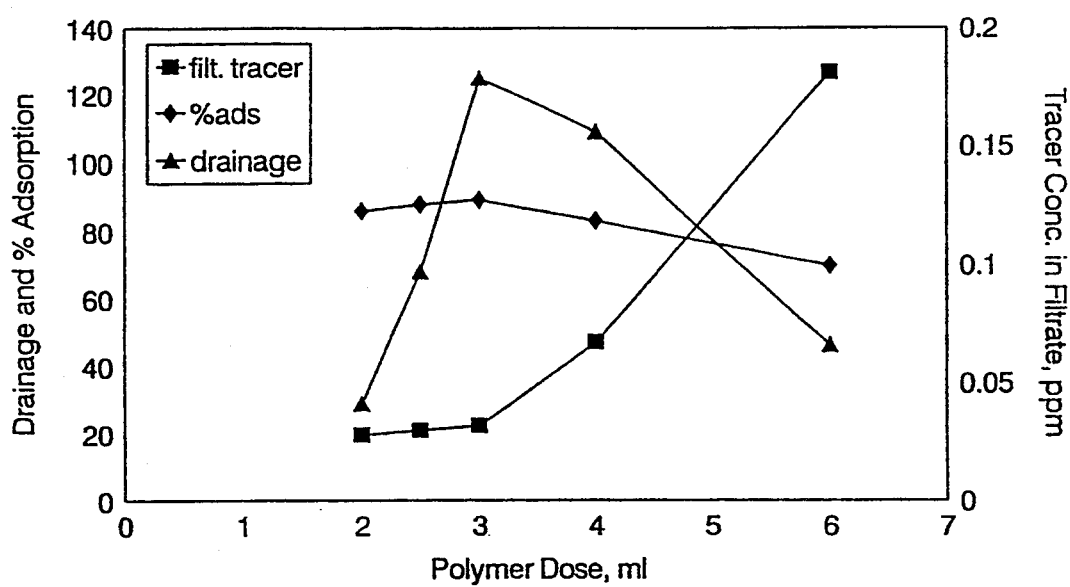
FIG. 8 is a graph comparing polymer dose to drainage and percentage adsorption for polymer B.
Figure 9:
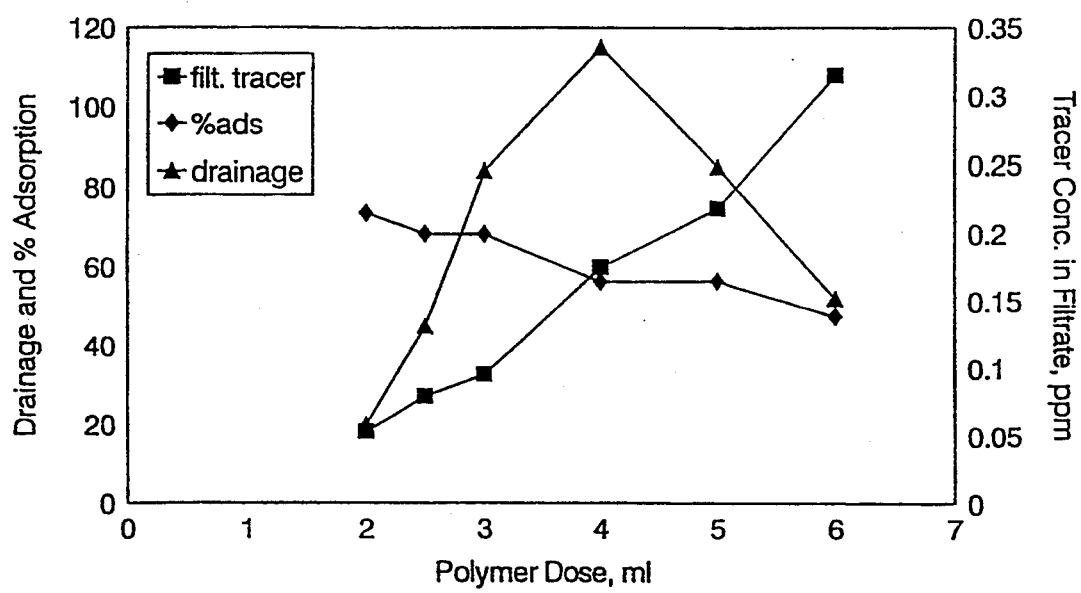
FIG. 9 is a graph comparing polymer dose to drainage and percentage adsorption for polymer B.
Figure 10:
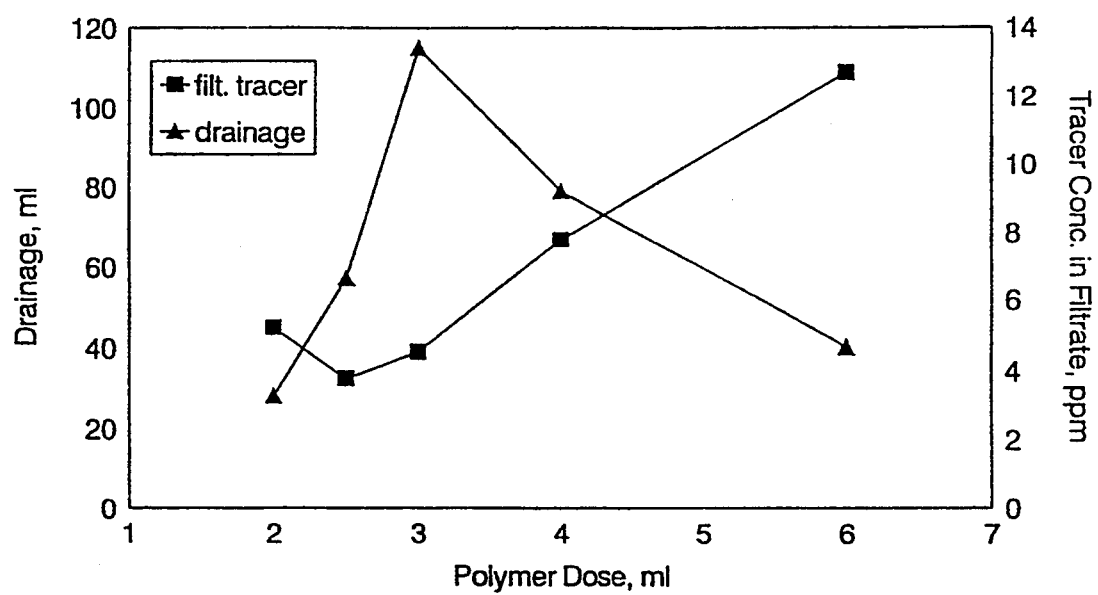
FIG. 10 is a graph comparing polymer dose to drainage and percentage adsorption for polymer B.
Figure 11:
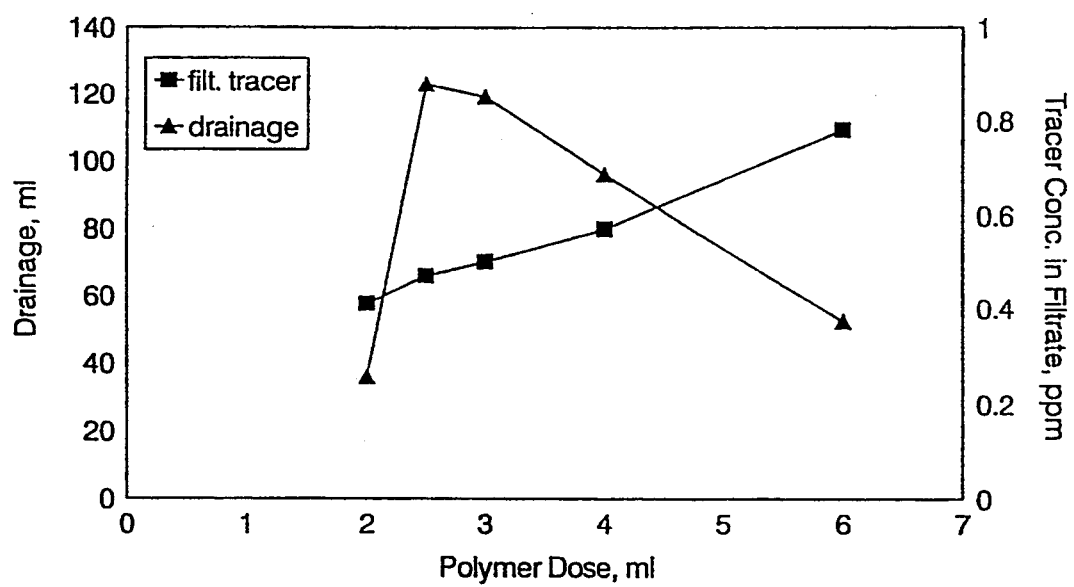
FIG. 11 is a graph comparing polymer dose to drainage and percentage adsorption for polymer B.
Figure 12:
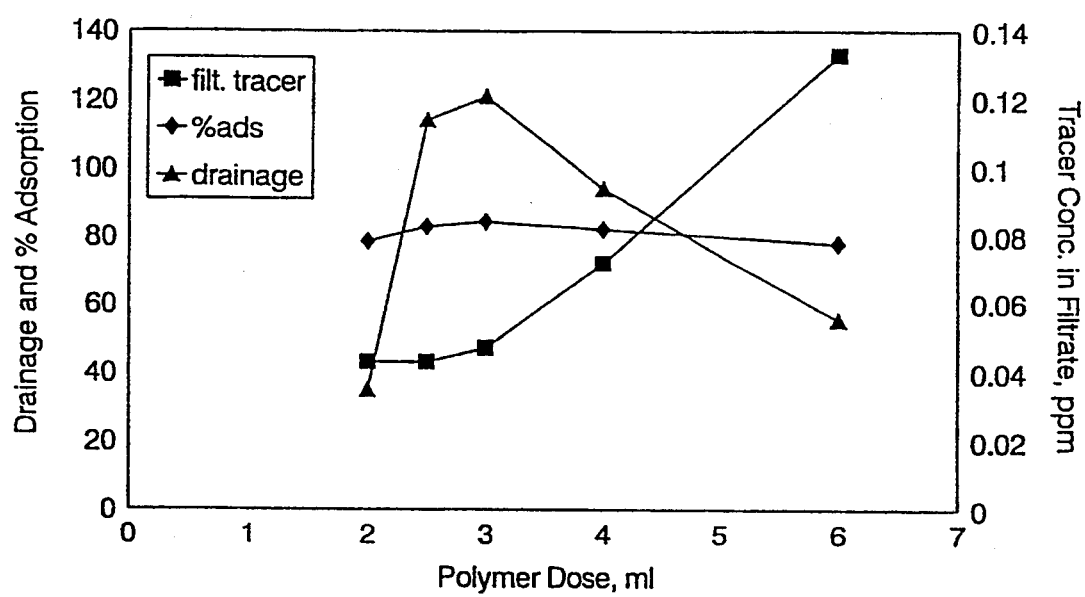
FIG. 12 is a graph comparing polymer dose to drainage and percentage adsorption for polymer B.
Figure 13:
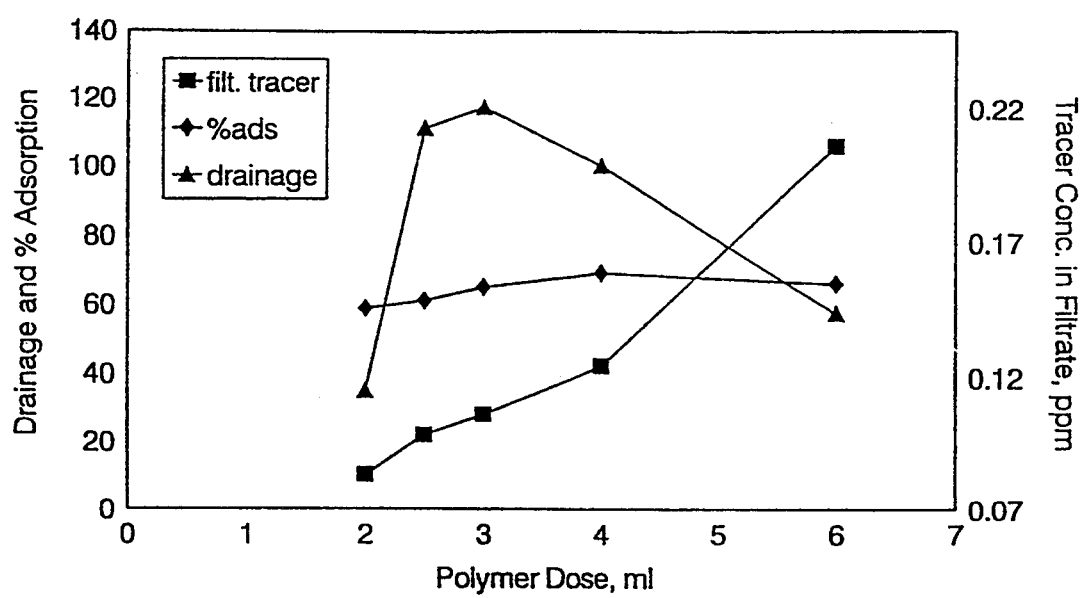
FIG. 13 is a graph comparing polymer dose to drainage and percentage adsorption for polymer B.

One aspect of the present invention provides a method for monitoring the performance of a polyelectrolyte using a tracer material which is oppositely charged compared to the polyelectrolyte. According to one embodiment of the invention, the tracer of the present invention interacts with the polyelectrolyte and partitions along with the polyelectrolyte between the surfaces of the solid particles or oil and the filtrate. It is believed that the interaction between the tracer and the polyelectrolyte forms a complex through electrostatic attraction. The surprising advantage of the present invention is that optimum polyelectrolyte dosage can be seen as a distinct break in the curve of tracer filtrate concentration values. Another surprising advantage of the invention, is that it had been thought that the addition of a compound of opposite charge to the polyelectrolyte would, in effect, deactivate that portion of the polyelectrolyte that serves to neutralize the tracer. In fact, we have found that such is not the case, and the addition of a tracer of opposite charge to the polyelectrolyte to form a complex does not lower or impede the activity or charge neutralization ability of the polyelectrolyte.

The tracer materials of the subject invention preferably have a charge which is opposite to the charge carried by the polyelectrolyte polymer that is being monitored. For example, cationic coagulants and flocculants are preferably monitored by an anionically charged tracer. Preferably, the tracer materials fluoresce at wavelengths detectable by instrumentation in real time, partition with the cationic polyelectrolyte, and are water soluble or dispersible in the water, emulsion, or sludge being treated. Examples of preferred materials useful in this invention include water soluble pyrene sulfonic acids including 1,3,6,8pyrenetetrasulfonic acid sodium salt (PTSA), 8-hydroxy 1,3,6-pyrene trisulfonic acid sodium salt, and pyrenesulfonic acid (mono) sodium salt. Other highly :polar, fluorescent, anionic materials which are substantially water soluble, would also be useful in this invention. While the materials of this invention are preferably used as alkali metal salts, and preferably sodium salt form, they may be also employed in the free acid form.

The anionic tracer materials useful in this invention are typically employed in the smallest amount which is measurable by fluorometers. Accordingly, the materials may be employed at levels of from as little as several parts per billion to equal parts based on the weight of the cationic polyelectrolyte used in the process. Generally, the anionic water soluble tracer materials are employed at a ratio of from about 1 part per billion to about 750,000 parts per million based on the polyelectrolyte used in the process. Preferably, the anionic water soluble tracer materials of this invention are employed at a rate of from about 10 parts per billion to about 500,000 parts per million based on the polyelectrolyte used in the process. Most preferably, the anionic water soluble tracer materials of this invention are employed at a rate of from about 100 parts per billion to about 200,000 parts per million based on the cationic polyelectrolyte used in the process.

According to another preferred embodiment of the invention, the tracer material used in the practice of the invention is one tracer selected from the group consisting of resazurin, Tinopal cbs-x (distyryl biphenyl derivative), and Tinopal rbs-200 (triazole-stilbene). Surprisingly, we have found the addition of suitable anionic tracer materials do not appear to interfere with, or consume the cationic charge on the polymer, so that all of the polymer is useful for its intended purpose. Nevertheless, the anionic tracer material is preferably added at dosages significantly less than that of the polymer.

Referring to the polymers and separation processes in more detail, the use of organic polymers for industrial and municipal coagulation and flocculation processes is an ever expanding technical field. Such polymers are commonly water-soluble or at least water dispersible at use concentration, contain electrolytic or at least high polar groups and frequently, but not necessarily, are wholly synthetic polymers, derivatives of natural polymers and/or biologically engineered polymers.

Solids in nature normally are negatively charged, as are emulsified droplets of oil-in-water emulsions. The electrostatic charge on a solid particle or droplet generally has a strong influence on its tendency to agglomerate or coalesce with neighboring particles or droplets. Other factors influence the tendency to agglomerate or coalesce, including particle/droplet size and/or density, the density of the continuous liquid phase, the mechanical forces to which the particle/droplet is subjected, such as agitation and shear forces, temperature, and the like.

Traditionally, coagulation is defined as a the process of reducing the surface charge (minimizing the electrostatic forces) on solids to the point where Van der Waals forces can predominate and cause agglomeration of the suspended particles. In emulsion breaking, coagulation is the process of neutralizing the surface charge on emulsified droplets and/or otherwise destabilizing the emulsion to the point where the droplets coalesce. Traditionally, flocculation is defined as the process of agglomeration of suspended solids in which no substantial change of surface charge has been accomplished. In emulsion breaking, flocculation is the process of agglomeration of dispersed droplets and/or solids in which no substantial change of surface charge has been accomplished. In either instance, coagulation often precedes flocculation and the solids/droplets being flocculated are coagulated solids/droplets.

Coagulating agents or coagulants are most frequently positively charged (cationic) chemical species, such as cationic polyelectrolyte. Flocculating agents (flocculants) are most frequently negatively-charged (anionic) chemical species such as anionic polyelectrolytes. Flocculants are believed to enhance agglomeration/coalescence through a bridging mechanism, adsorbing onto a plurality of particles/droplets and physically holding them together. One or more adsorption mechanisms may come into operation in a flocculation process. Traditionally, polyelectrolyte coagulants are of relatively low molecular weight, for instance with a weight average molecular weight range of 200 to 500,000, while polyelectrolyte flocculants typically have a weight average molecular weight of at least 1,000,000, or 5,000,000, at times much higher, water solubility or dispersibility being the limiting factor. There is now an increased use of relatively high molecular weight cationic polyelectrolytes in solid/fluid or fluid/fluid separation processes, which cationic polyelectrolytes are at times referred to as cationic flocculants. It is now generally accepted that most cationic polyelectrolytes will not only neutralize surface charges but also provide some bridging between partides/droplets, unless the polyelectrolyte is of extremely low molecular weight, and that the dual coagulant/flocculant characteristic of cationic polyelectrolyte is merely less conspicuous when the polyelectrolyte is within the traditional coagulant molecular weight range.

Cationic polyelectrolytes are thus currently used in water treatment applications as coagulants, in which their use may or may not be followed by an anionic flocculant; as dual coagulant/flocculants, which may or may not be preceded by a cationic coagulant and/or followed by an anionic flocculant; and as flocculants, which may or may not be preceded by a cationic coagulant. The blurring of traditional demarcations between coagulants and flocculants may indicate that the earlier classifications of polyelectrolytes were behind the current level of polymer science.

Water soluble cationic coagulants are well known, and commercially available. Many water soluble cationic coagulants are formed by condensation polymerization. Examples of polymers of this type include epichlorohydrin-dimethylamine, and epichlorohydrin-dimethylamine-ammonia polymers which are exemplified in U.S. Pat. No. Re. 28,807 and U.S. Pat. No. Re. 28,808 both of which are hereinafter incorporated by reference into this specification. Additionally, cationic coagulants may include polymers of ethylene dichloride and ammonia, or ethylene dichloride and dimethylamine, with or without the addition of ammonia. Additional polymers which may be used as cationic coagulants include condensation polymers of multifunctional amines such as diethylenetriamine, tetraethylenepentamine, hexamethylenediamine and the like with ethylenedichloride, or condensed onto themselves. Examples of polymers of this type are known in the art. Other polymers made by condensation reactions such as melamine formaldehyde resins may also be employed as cationic coagulants in this invention.

Additional cationic coagulants include cationically charged vinyl addition polymers such as polymers and copolymers of diallyldimethylammonium chloride, dimethylaminoethylmethacrylate, dimethylaminomethylmethacrylate methyl chloride quaternaries, methacrylamidopropyltrimethylammonium chloride, (methacryloxyloxyethyl)trimethyl ammonium chloride; diallylmethyl(betapropionamido)ammonium chloride; (beta-methacryloxyloxyethyl)trimethylammonium methylsulfate; quaternized polyvinyllactam; dimethylaminoethylacrylate and its quaternary ammonium salts; and acrylamide or methacrylamide which has been reacted to produce the Mannich or quaternary Mannich derivative. The molecular weights of these cationic polymers, both vinyl addition and condensation, range from as low as several hundred to as high as one million. Preferably, the molecular weight range should be from several thousand to 750,000. Often the choice of upper molecular weight is made upon a cost basis since higher molecular weight vinyl addition polymers are often more expensive. Upper level molecular weight should not be limiting so long as the polymer remains soluble or partially soluble in the water into which it is placed. Preferred polymers for use in the practice of our invention include dimethylamine-epichlorohydrin copolymers. It should be pointed out that the above listing of polymers that may be used for the synthetic cationic organic polyelectrolyte coagulant of this invention is by no means inclusive and is not meant to be limiting as to the application of our invention.

As stated above, the synthetic polyelectrolyte flocculants useful in the practice of the invention may be anionic or cationic. The choice of flocculant is often process dependent and will be readily discoverable through simple testing of the water or emulsion to be treated. Suitable cationic flocculants for use in this invention generally have molecular weights in excess of 1,000,000 and often 20,000,000. These types of polymers are normally prepared by vinyl addition polymerization of a cationic vinyl monomer, or the copolymerization of a cationic vinyl monomer with either a nonionic monomer such as acrylamide or methacrylamide to produce a cationically charged polymer, or the cationic monomer may be reacted with an anionically charged vinyl addition monomer so as to produce an amphoteric polymer.

Suitable cationic vinyl addition monomers include: diallyldimethylammomum chloride; dimethylaminoethylmethacrylate; dimethylaminoethylmethacrylate methyl chloride quaternary; methacrylamidopropyltrimethylammonium chloride; dimethylaminiomethylmethacrylate; and other cationic vinyl addition monomers. While the polymer may be formed as a cationic polymer, it is also possible to react certain non-ionic vinyl addition polymers to produce cationically charged polymers. Polymers of this type include those prepared through the reaction of polyacrylamide with dimethylamine and formaldehyde to produce a Mannich derivative.

Suitable anionic flocculants for use in the practice of this invention include polymers and copolymers of acrylic acid, methacrylic acid, acrylamidomethylpropane sulfonic acid, N-vinyl formamide, acrylamide, and polymers.

As stated earlier, the invention is directed to solids/liquid or liquid/liquid separation techniques in which the separation process is aided by a natural or synthetic polyelectrolyte coagulant, flocculant, or both. Preferable applications of the invention include color removal and water clarification, sludge dewatering, and emulsion breaking.

Color removal and water clarification involve similar processes. Color is one of the indirect and nonspecific measures of organics in water and is reported in APHA units related to a platinum standard. A color value is a rough or approximate measure of the concentration of tannin, lignin, and other humic matter (commonly derived from partially decomposed plant matter) or other colored material in waters such as pulp/papermill wastewaters, textile wastewaters, other industrial wastewaters (particularly from industries employing partially decomposed plant and/or animal matter, surface waters, and other waters).

For the most part, color in water is a mixture of suspended solids, colloidal solids and dissolved solids (solutes) that possess a coloration characteristic, that is emit and/or reflect light with the visible wavelength region. Colored substances in waste water are largely organic compounds that represent breakdown products of high molecular weight substances produced by living cells. These substances are mainly anionic or nonionic polymers, and include humic acid, polysaccharides, polypeptides, lignins and tannins. Color values from about 1 to 50 or higher are not uncommon in surface waters and much higher color values are routinely seen in papermill wastewaters. Some of these organic materials are truly water soluble, and their removal from water requires precipitation, converting the solutes to colloidal and/or suspended solids forms(s). Some colored material, and generally all of the humic material, is present in water in colloidal form and is removed by coagulation. Colored suspended solids are removed by settlement.

Wastewater streams commonly have higher concentrations of suspended solids than raw water. The filtrate standards for wastewater color removal processes are often less stringent as to residual solids, but to protect the environment and to increase the recycling potential, the attainment of higher standards is routinely being sought. Historically hydraulic mixing was used in wastewater color removal processes, and currently the mixing equipment used is approaching that of raw water clarification plants. The extent of color removal by a chemical program is conventionally determined by colorometric analysis. Analysis for specific organic species in water usually requires sophisticated procedures and equipment.

According to one aspect of the invention, the invention is directed to optimizing coagulation and color removal processes using synthetic cationic polyelectrolytes and an anionic tracer. The polyelectrolyte and tracer form a complex. This allows the measurement of polyelectrolyte polymer which leaves the process with the aqueous effluent. Detecting the tracer/polymer complex in the effluent water indicates overfeeding of the polyelectrolyte polymer or a polymer which is not effectively coagulating the colored species in the water.

When the solids of a solids/liquid admixture are the predominant species, or approach predominance in the admixture, the separation processes employed are referred to as liquid/solids separation processes, and these include solids thickening and dewatering by gravity, sedimentation, flotation, centrifugation and filtration. These liquid/solids separation processes are used to remove water from sludge. Sludge is the concentrated waste effluent produced by water and sewage treatment processes.

Sludge dewatering processes commonly employ polymeric dewatering enhancing additives such as coagulants and flocculants to heighten the degree of solids concentration and speed at which such concentration occurs, and thus the separation of the water from the solids. Particles of solids generally have negative surface charges, causing them to repel neighboring particles and deterring the formation of larger particle masses. This resistance to mass formation and settling is a particularly serious problem for colloids. (Colloids are solids that are not captured by filtration through a 0.45 micron filter membrane in comparison to suspended particles which would be captured, and solutes which are dissolved and thus do not have any effective surface until precipitated.) Coagulants act by neutralizing such negative surface charges, destabilizing colloids, while flocculants attach to particle surfaces, bridging particles together to form flocs. The techniques of coagulation and flocculation are somewhat overlapped particularly when polyelectrolytes are employed for each mechanism.

In a polyelectrolyte-enhanced sludge dewatering process, the portion of the polyelectrolyte added that is effective in enhancing the dewatering performance is that portion that attaches to the solid particles. Polyelectrolyte that leaves the dewatering process with the water fraction has not enhanced the process efficiency. If the polyelectrolyte being added is very effective for the given sludge, the polyelectrolyte that leaves the water fraction generally represents an overdosage. More polyelectrolyte was added than required. If the polyelectrolyte being added is not very effective for the given sludge, the significant amount that typically leaves the process with the water fraction is an indication of the polyelectrolyte's performance deficiencies. In either instance, a determination of the amount of polyelectrolyte that leaves a dewatering process with the filtrate (water fraction) would be extremely beneficial. An effective polyelectrolyte should be added to a dewatering process in an amount just at or above that consumed by attachment to the solids surfaces. Whether the dosage selected approaches this optimal dosage could be determined, and the dosage adjusted if necessary, by detecting the level of the polyelectrolyte/tracer complex in the filtrate.

An emulsion is a dispersion of two or more mutually insoluble liquid phases, for instance water and oil., one liquid phase being dispersed in the other. Cationic coagulants typically find utility in the treatment of oily waste waters wherein oil is emulsified in water as an oil-in-water or "o/w" emulsion. An oily wastewater emulsion might contain any of various types of oils in a wide range of concentrations. These oils are sometimes defined as substances that can be extracted from water by hexane, carbon tetrachloride, chloroform, or fluorocarbons. The types of oils found in these emulsions depend in part upon the industry or other activity from which these emulsions are produced, and include animal fats, vegetable oils, lubricants, cutting fluids, heavy hydrocarbons such as tars, grease, crude oils and diesel oils, light hydrocarbons such as gasoline, kerosene and jet fuel, and the like. Their concentration in oily wastewater may vary from only a few parts per million by volume to as much as about 5 to 10 percent by volume. Some waste emulsions may in fact contain over 10 percent by volume oil. In addition to the oils, typical contaminants of these emulsions include matter present as insoluble solids, as solutes and/or in colloidal form, including silt, metal particles, grit, metal fines, carbon, paint pigments, soot, corrosion products, soaps, emulsifiers, cleaners, surface active compounds, solvents, and other residues. A stable o/w emulsion is a colloidal system of electrically charged oil droplets surrounded by an ionic environment. The emulsion may be stabilized by mixing and shearing, surfactants and fine, solid particles.

The treatment of oily wastewaters often includes both coagulation and flocculation. The coagulation destroys the emulsifying properties of any emulsion-stabilizing surface active agent and/or neutralization of the charged oil droplet. Flocculation agglomerates the neutralized droplets into large separable globules or flocs. Some of the organic polymeric emulsion breakers used in o/w emulsion treatment programs include without limitation, cationic polyamines, cationic polyacrylates and their substituted copolymers.

Irrespective of the particular process involved, the unifying feature which allows the subject of this invention to be applicable to a variety of processes is that the cationic or anionic polyelectrolyte, if properly dosed, is consumed in the process, and does not leave with the "purified" effluent. Thus, in color removal, the polyelectrolyte remains with the materials that caused the color; in water clarification, the polyelectrolyte remains with the inorganic materials being removed from the water; in sludge dewatering the polyelectrolyte remains with the sludge; and, in the breaking of oil-in-water emulsions, the polyelectrolyte remains with the recovered oil. Whether the polyelectrolyte is in the effluent is determined by monitoring the appearance a polyelectrolyte/tracer complex in the effluent. If the complex appears, either too much polyelectrolyte is being added to the process or the polyelectrolyte is not reacting as intended with electrolyte species the water treatment process operator wishes to remove from the process. Of course, other processes involving polyelectrolytes are analogous, and the process of the instant invention should also perform in other applications where a polyelectrolyte polymer is consumed.

The following examples are presented to describe preferred embodiments and utilities of the invention and are not meant to limit the invention unless otherwise stated in the claims appended hereto.

EXAMPLE 1

Sludge Dewatering

Three Pyrensulfonic acid compounds were evaluated on a sludge obtained from a papermill in the Pacific Northwest. The compounds were 1,3,6,8-Pyrenetetrasulfonic acid sodium salt (PTSA), 8-Hydroxy 1,3,6-Pyrene trisulfonic acid sodium salt, and Pyrenesulfonic acid (mono) sodium salt. Each of these compounds was evaluated in the fixed and continuous modes with 20 mole percent of a quaterinized dimethylaminoethylacrylate methyl chloride quat DMAEM.MCQ/Acrylamide copolymer (Polymer A). In the fixed mode, the agent is mixed with the wastewater prior to conditioning with the polymer. In the continuous mode, the agent is mixed with the product solution. The results are shown in FIGS. 1–6. As can be seen, all of the compounds worked well in monitoring the product's performance as measured by the drainage of the conditioned sludge and filtrate tracer concentration. This testing suggests that Pyrenesulfonic acid compounds with several degrees of charge density work well with high charged polymer such as 20 mole % DMAEM.MCQ. Several different chemistries of fluorescent species were evaluated on municipal sludge obtained from a municipal wastewater treatment plant. The species evaluated were:

Fluorescein
Anthracenesulfonic acid
Resazurin
Tinopal CBS-X (Distyryl biphenyl derivative)
7-Amino 1,3-Naphthalene disulfonic acid (Amino G Acid)
3,4,9,10-Perylenetetracarboxylic acid
Tinopal RBS-200 (Triazole-Stilbene)

All of the species were evaluated in the continuous mode by mixing the probe with one percent solution of (Polymer B). The results are shown in FIGS. 7–13. All of the above species except 3,4,9,10-Perylenetetracarboxylic acid; 7-Amino 1,3-Naphthalene disulfonic acid; Anthracenesulfonic acid; and Fluorescein showed good drainage results with Polymer B. The results suggest that many more species can be used for sludge dewatering process control and are not limited to PTSA.

Figure 14:
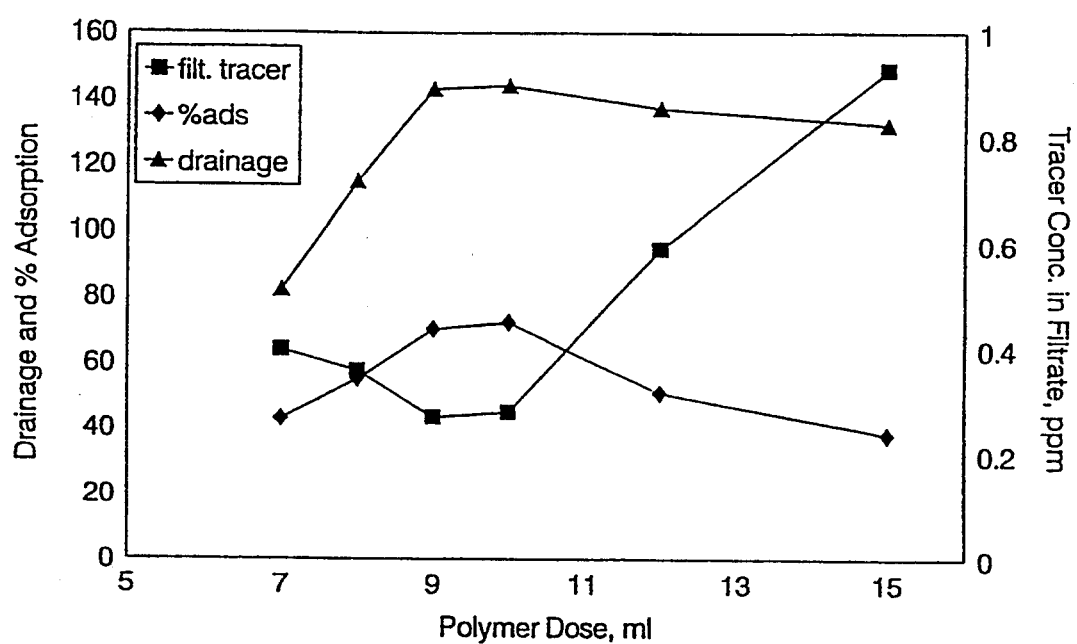
FIG. 14 is a graph comparing polymer dose to drainage and percentage adsorption for polymer B.

PTSA was evaluated on a textile mill sludge obtained from a southern, U.S. Textile Plant. PTSA was evaluated in a continuous mode at 2000 ppm in Polymer B. The results, as shown in FIG. 14, indicate that the PTSA concentration in the filtrate is followed well with sludge drainage.

Figure 15:
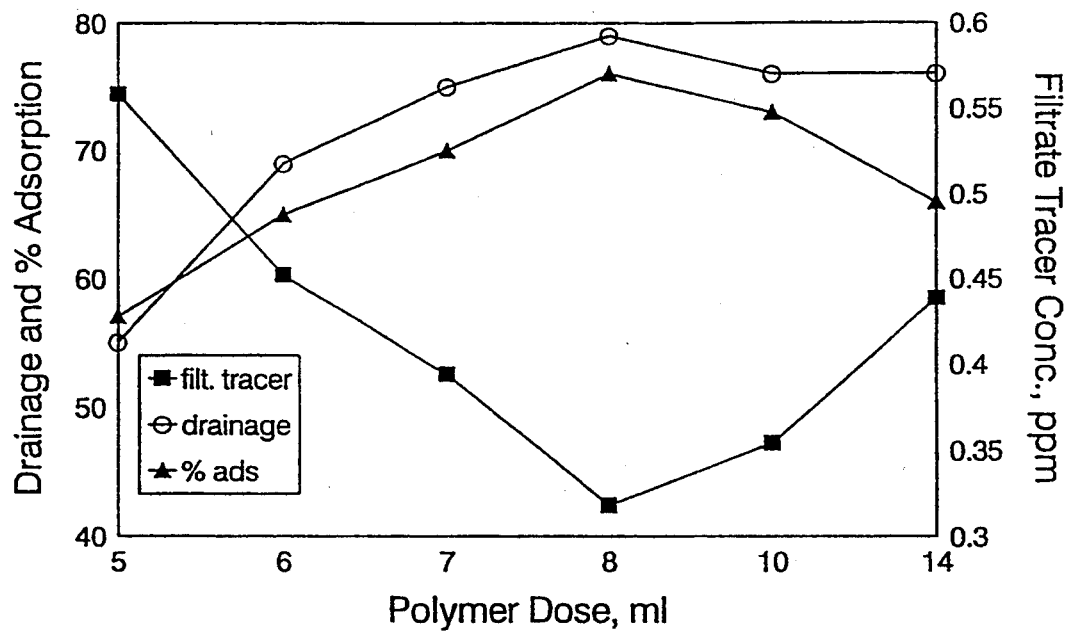
FIG. 15 is a graph comparing polymer dose to drainage and percentage adsorption for polymer B.
Figure 16:
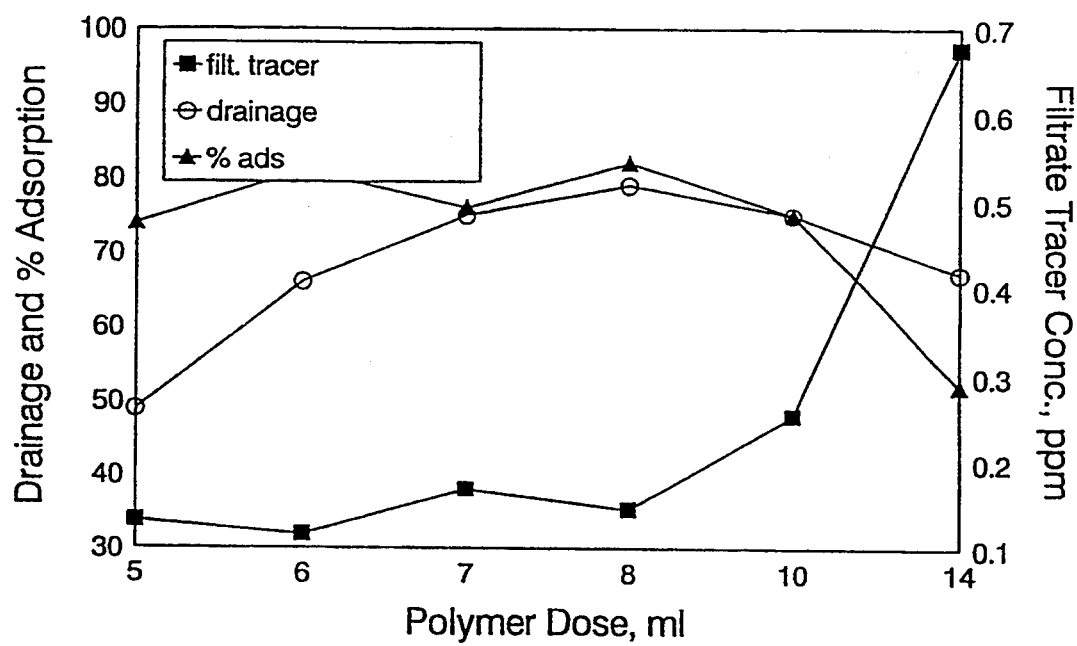
FIG. 16 is a graph comparing polymer dose to drainage and percentage adsorption for polymer A.
Figure 17:
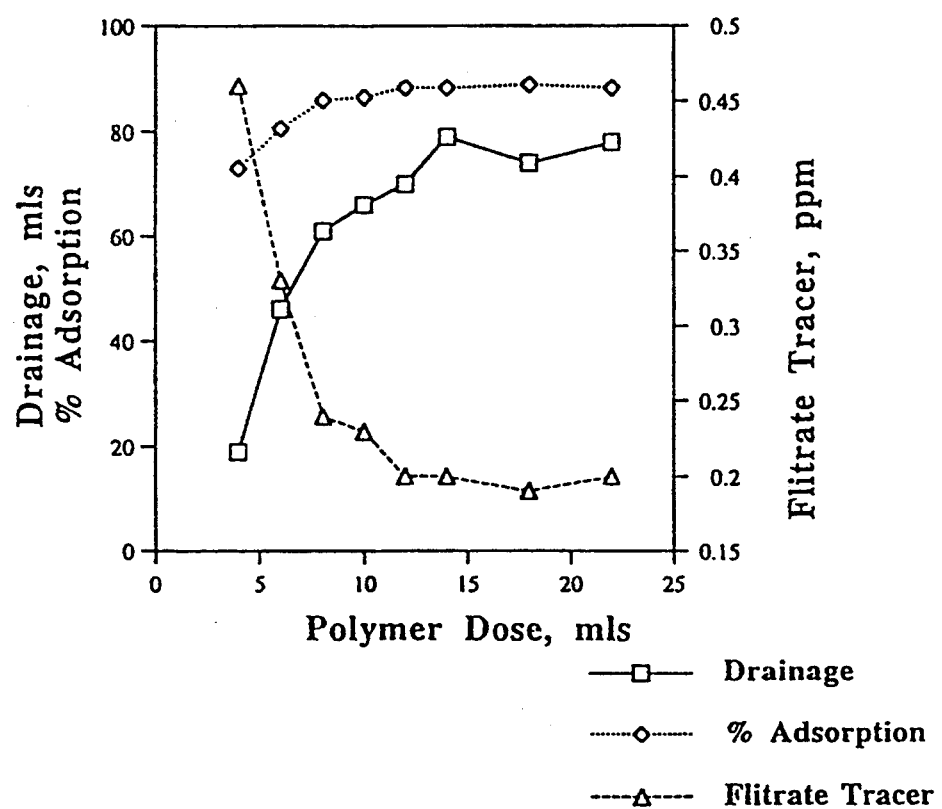
FIG. 17 is a graph comparing polymer dose to drainage and percentage adsorption for polymer C.
Figure 18:
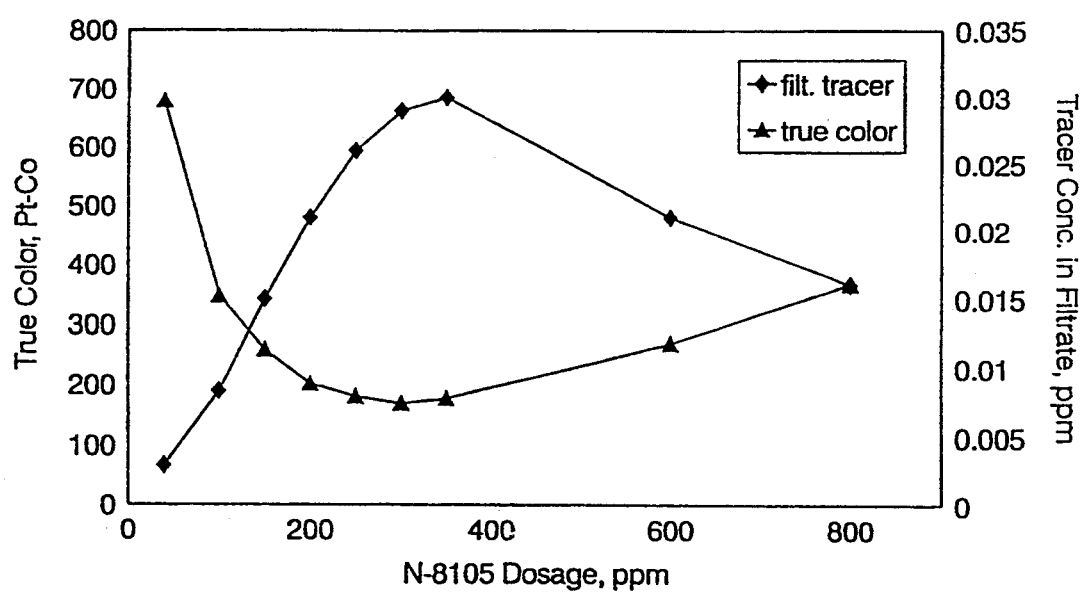
FIG. 18 is a graph comparing the dosage of polymer D to the amount of color removal.
Figure 19:
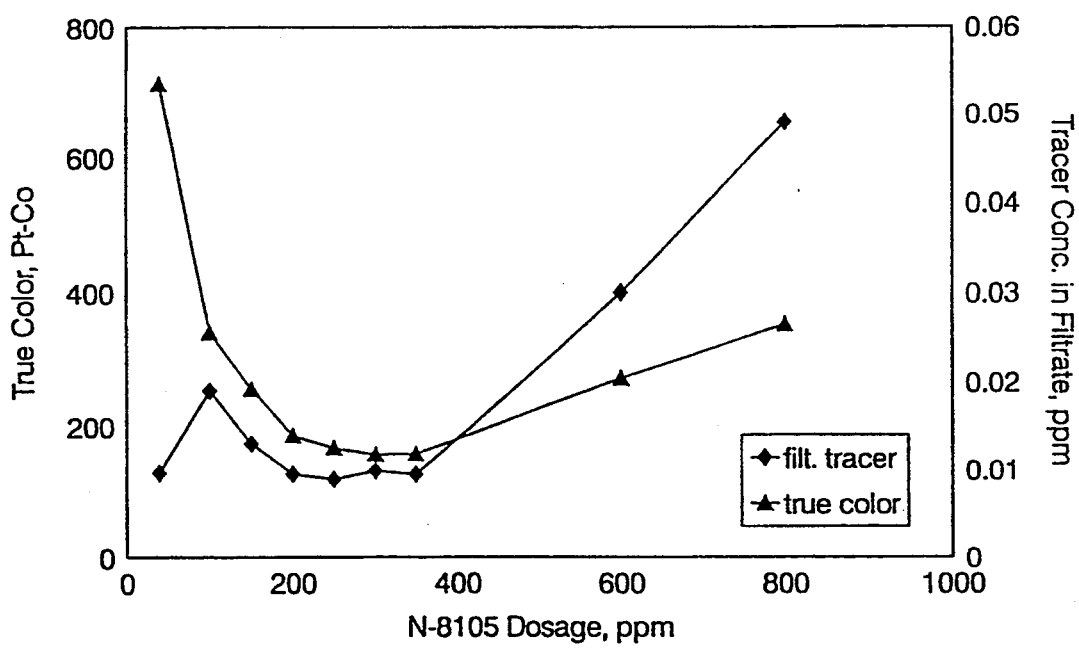
FIG. 19 is a graph comparing the dosage of polymer D to the amount of color removal.
Figure 20:
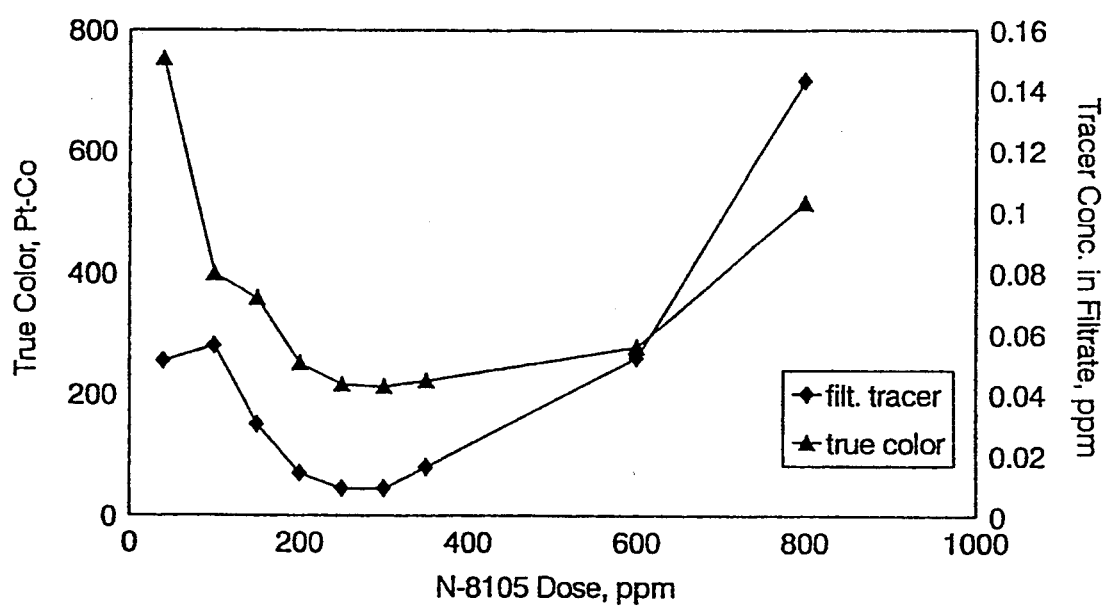
FIG. 20 is a graph comparing the dosage of polymer D to the amount of color removal.
Figure 21:
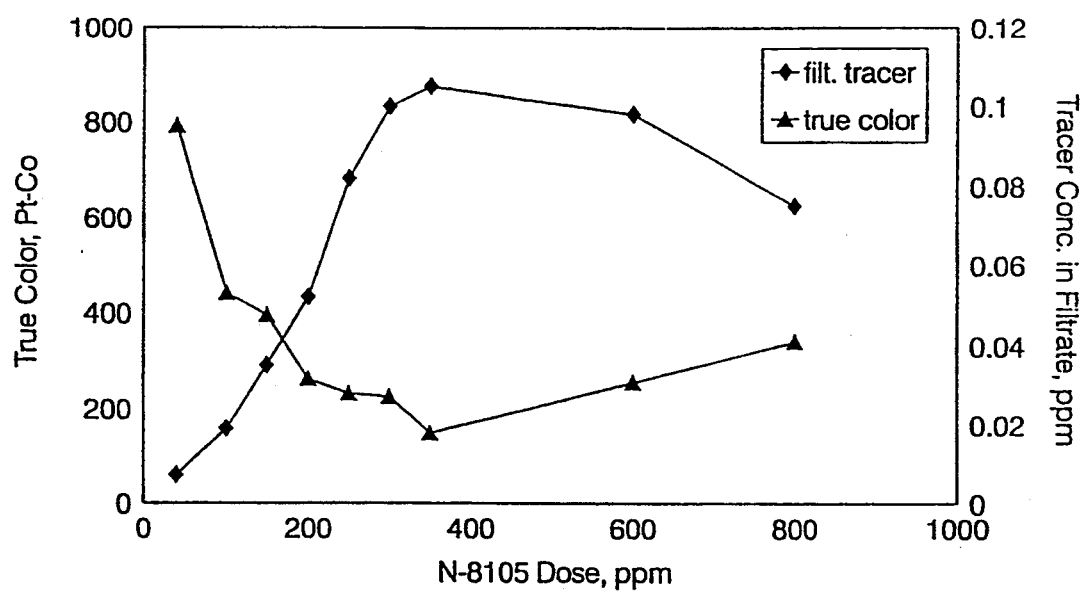
FIG. 21 is a graph comparing the dosage of polymer D to the amount of color removal.
Figure 22:
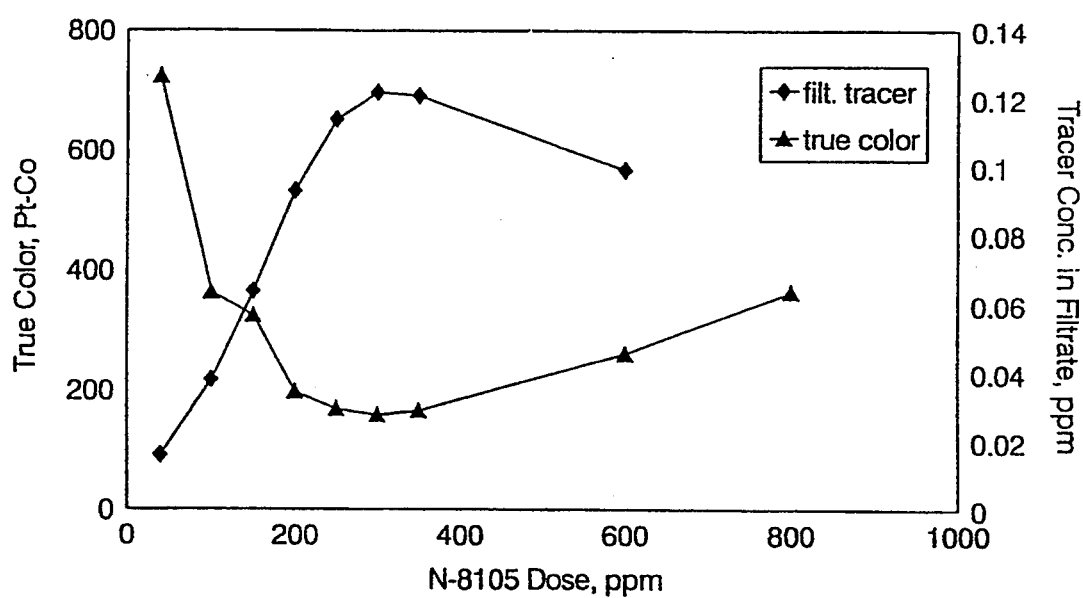
FIG. 22 is a graph comparing the dosage of polymer D to the amount of color removal.
Figure 23:
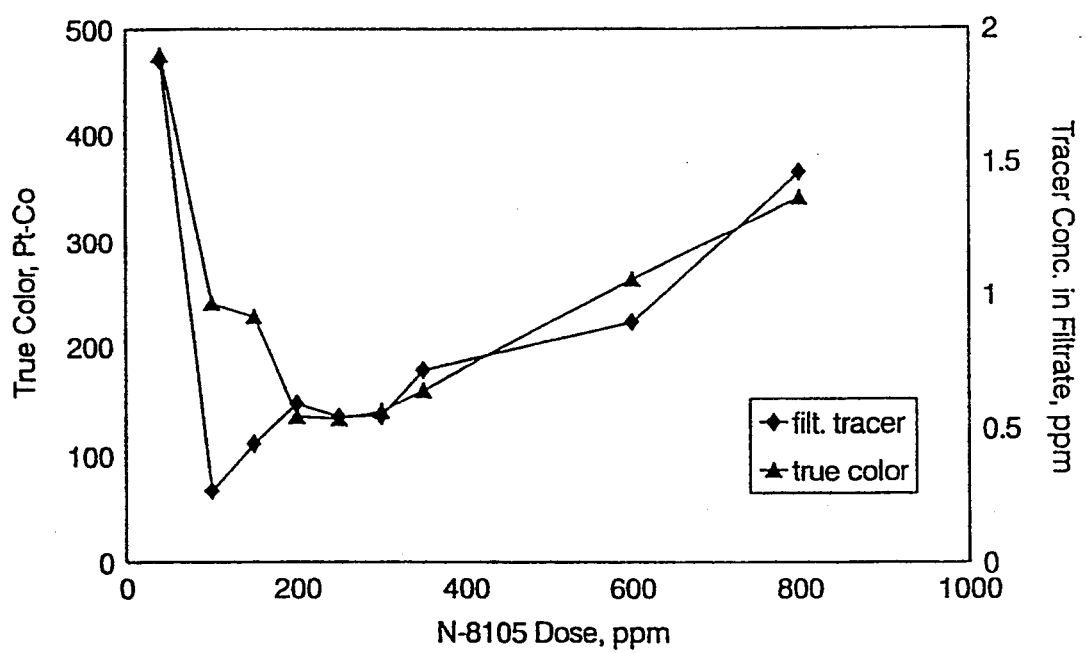
FIG. 23 is a graph comparing the dosage of polymer D to the amount of color removal.
Figure 24:
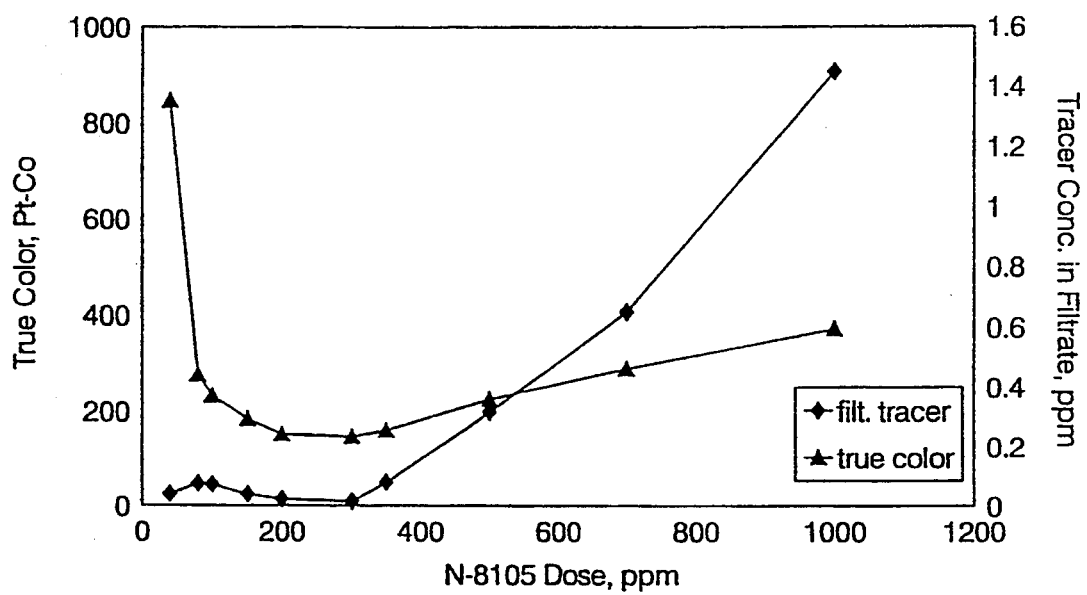
FIG. 24 is a graph comparing the dosage of polymer D to the amount of color removal.

Similar evaluation with PTSA on sludge from an additional paper mill in the Pacific Northwest and from a Wisconsin paper mill also showed good correlation between product performance as measured by the sludge drainage and filtrate tracer concentration. The results are shown in FIGS. 15–17. Polymer A (20 mole % DMAEM.MCQ/Acrylamide copolymer) was used for conditioning the Pacific Northwest paper mill sludge and polymer C, (a DMAEM.MCQ/Acrylamide copolymer) was used for conditioning the Wisconsin sludge.

EXAMPLE 2

Color Removal

The following agents were evaluated on inlet basin wastewater samples received from a Florida paper mill.
1,3,6 Naphthalenetrisulfonic Acid, Sodium Salt
1,5 Naphthalenedisulfonic Acid, Sodium Salt (NDSA)
Naphthalenesulfonic Acid, Sodium Salt
1,3,6,8-Pyrenetetrasulfonic Acid, Sodium Salt (PTSA)
8 Hydroxy 1,3,6 Pyrenetrisulfonic Acid, Sodium Salt
1 Pyrenesulfonic Acid, Sodium Salt
Resazurin
Tinopal CBS-X (Distyryl biphenyl derivative)

All of these agents were evaluated by mixing each agent at 200 to 2000 ppm by weight with Polymer D (Epi-DMA polymer). A ten percent solution of the tracer containing product was used for color removal experiments. The sample of wastewater was mixed with the tracer containing Polymer D solution in a series of beakers at several dosages. Once the product is added to the beaker, the wastewater is stirred at 80 rpm using a Phipps and Bird gang stirrer for one minute, followed by five minutes of mixing at 20 rpm. All the beakers containing wastewater were then allowed to settle for 10 minutes (no stirring). At the end of the settling period, a sample of supernatant was drawn from each beaker and filtered through a 0.8 micron filter. The tracer concentration in the filtered sample was measured by a fluorometer. In addition, the true colors of the supernatant samples were measured. The true color and filtrate tracer concentration were plotted against Polymer D dose. The results are shown in FIGS. 18–24. The results clearly show excellent correlation between the true color and the filtrate tracer concentration. All of the agents except Pyrenesulfonic acid, sodium salt and Tinopal CBS-X showed excellent correlation between color and tracer concentration. With Pyrenesulfonic acid, sodium salt and Tinopal CBS-X, the treated wastewater samples did not show any significant fluorescence at the specific wavelengths for these compounds.

Figure 25:
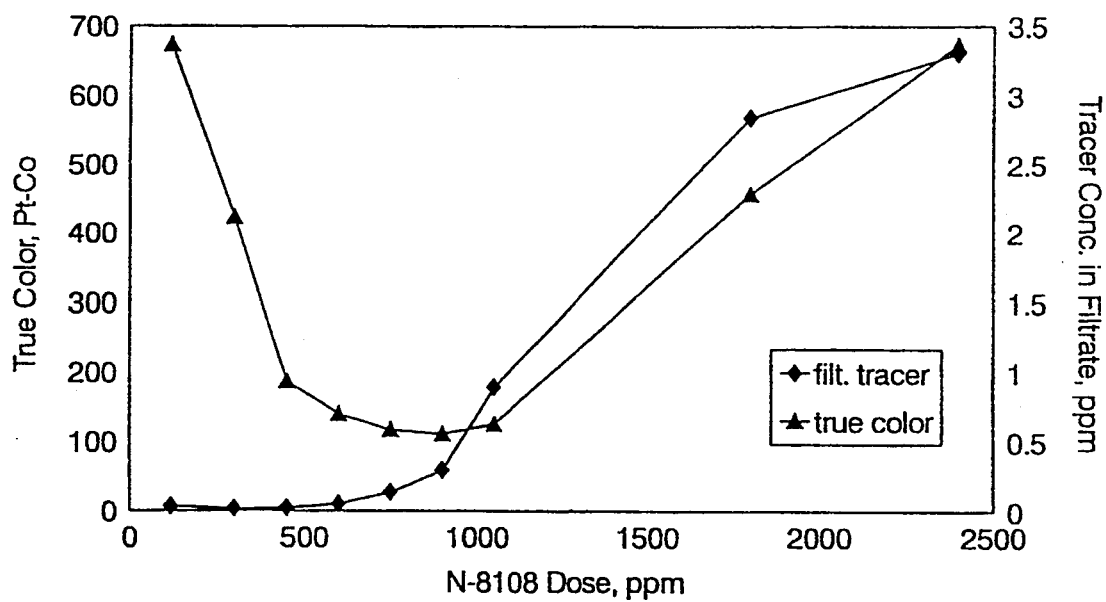
FIG. 25 is a graph comparing the dosage of polymer D to the amount of color removal.

Pyrene Tetrasulfonic acid, sodium salt, was also evaluated on the Florida inlet basin wastewater using another polymer. DADMAC polymer Polymer E was used for color removal instead of Polymer C. The results, as shown in FIG. 25, demonstrate that the tracer can monitor the product performance and is not specific to the chemistry of the polymer.

These experiments confirmed that the anionic tracers can be successfully used to monitor a product's performance in color removal applications. This technique can be used on-line for product dose optimization and control.

EXAMPLE 3

Sludge Dewatering

Figure 26:
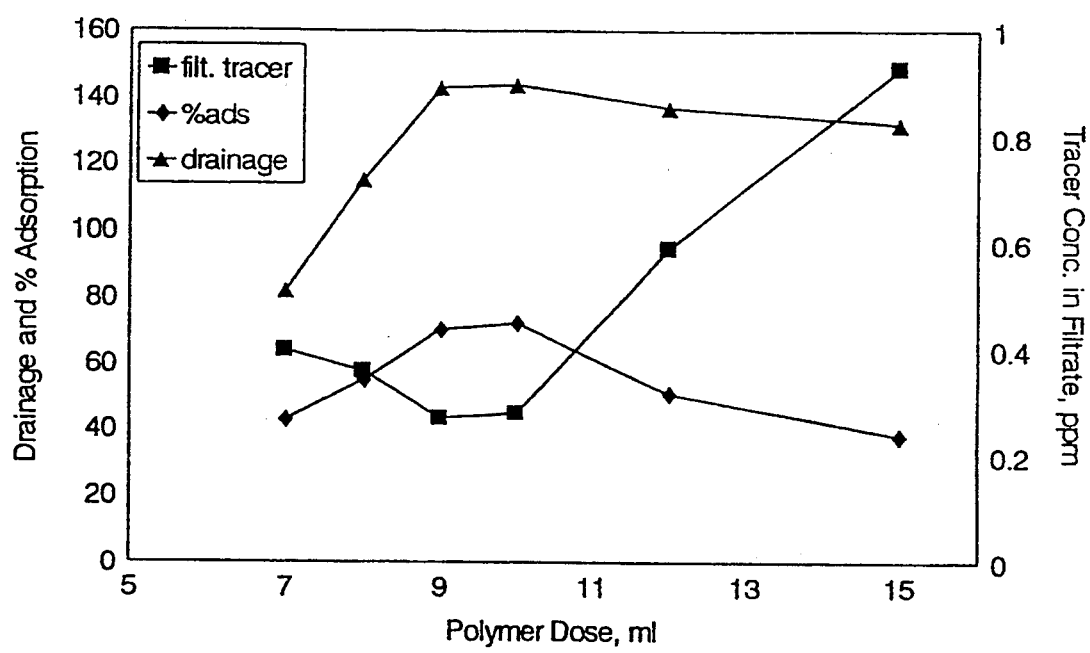
FIG. 26 is a graph comparing polymer dose to drainage and percentage adsorption for polymer A.

A textile mill sludge containing approximately 3.0 percent solids was treated with several dosages of 1.0 percent solution of Dimethylaminoethylacrylate methyl chloride quat(DMAEA. MCQ)-Acrylamide copolymer which contained 20 ppm Pyrenetetrasulfonic acid. The copolymer used was in the latex form and had 1 percent solids with an RSV range of 13 to 21. The Pyrenetetrasulfonic acid tracer was mixed with one percent solution of the copolymer to obtain 20 ppm of tracer in the solution. The standard free draining test was conducted at several dosages of this polymer-tracer solution and the water drainage was recorded at 10 seconds after the treated wastewater is poured through the fabric filter. The filtrate samples were collected and were analyzed for PTSA concentration by fluorescence technique. FIG. 26 shows a plot of water drainage, % adsorption and tracer concentration in the filtrate against polymer dose in milliliters (ml) of one percent solution. The results showed that as polymer dose is increased from 7 milliliters to 9 milliliters, the water drainage increased from about 80 ml to 150 ml. Further increase in the polymer dose decreased the water drainage. Therefore the optimum polymer dose was 9 ml of polymer solution.

The filtrate tracer concentration shown on FIG. 26 also reflected the optimum dose. The filtrate tracer concentration was minimum at optimum dose and significantly higher at higher polymer dose.

EXAMPLE 4

Sludge Dewatering

Figure 27:
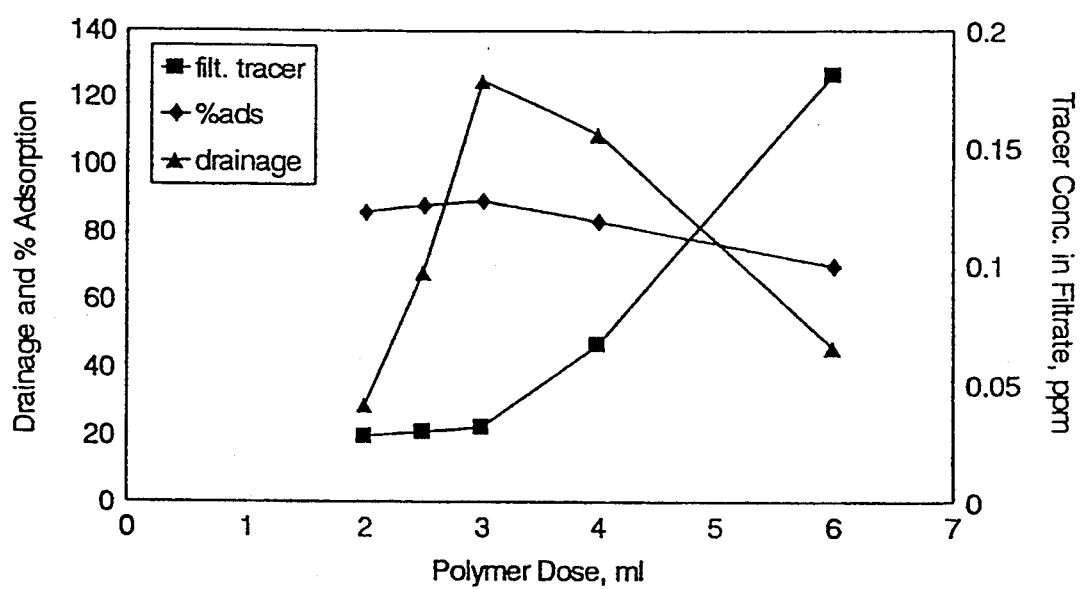
FIG. 27 is a graph comparing polymer dose to drainage and percentage adsorption for polymer A.

A municipal sludge containing approximately 2.0 percent solids was treated with several dosages of 1.0 percent solution of Dimethylaminoethylacrylate methyl chloride quat(DMAEA. MCQ)-Acrylamide copolymer which contained 20 ppm Distyryl biphenyl derivative (Trade Name Tinopal CBS-X). The copolymer used was in the latex form and had 31 percent solids with RSV range of 13 to 21. The tracer was mixed with one percent solution of the copolymer to obtain 20 ppm of tracer in the solution. The standard free draining test was conducted at several dosages of this polymer-tracer solution and the water drainage was recorded at 10 seconds after the treated wastewater is poured through the fabric filter. The filtrate samples were collected and were analyzed for PTSA concentration by fluorescence technique. FIG. 27 shows a plot of water drainage, % adsorption and tracer concentration in the filtrate against polymer dose in milliliters (ml) of one percent solution. The results showed that as polymer dose is increased from 2 milliliters to 3 milliliters, the water drainage increased from about 25 ml to 130 ml. Further increase in the polymer dose decreased the water drainage. Therefore the optimum polymer dose was 3 ml of polymer solution.

The filtrate tracer concentration shown on FIG. 27 also reflected the optimum dose. The filtrate tracer concentrations remained low until the optimum dose and increased significantly at higher polymer dosages.

EXAMPLE 5

Sludge Dewatering

Figure 28:
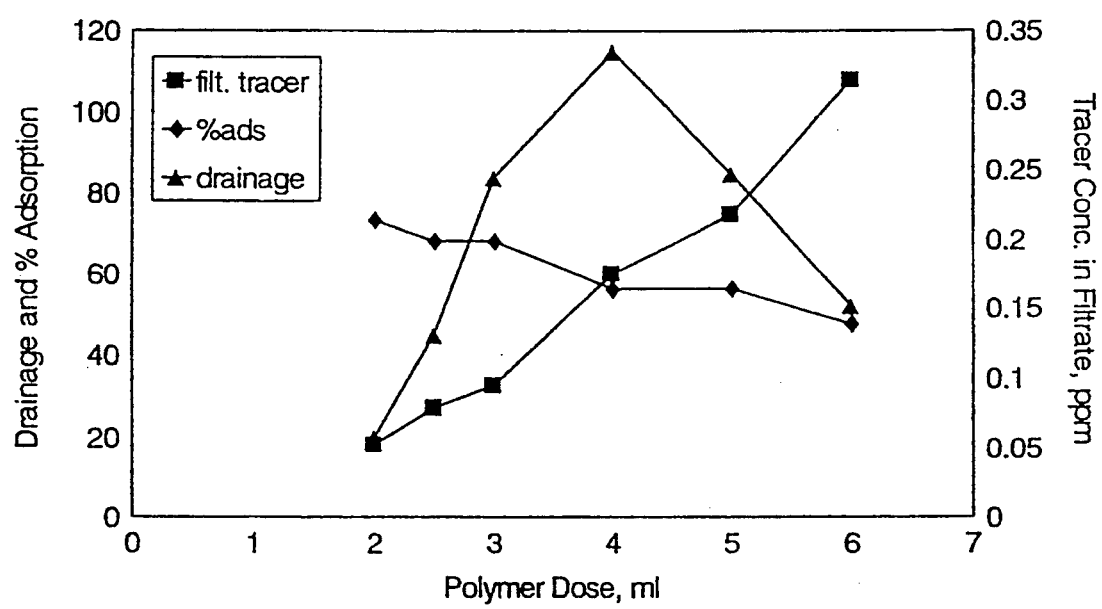
FIG. 28 is a graph comparing polymer dose to drainage and percentage adsorption for polymer A.

A municipal sludge containing approximately 2.0 percent solids was treated with several dosages of 1.0 percent solution of Dimethylaminoethylacrylate methyl chloride quat(DMAEA. MCQ)-Acrylamide copolymer which contained 20 ppm Anthracenesulfonic acid. The copolymer used was in the latex form and had 31 percent solids with RSV range of 13 to 21. The tracer was mixed with one percent solution of the copolymer to obtain 20 ppm of tracer in the solution. The standard free draining test was conducted at several dosages of this polymer-tracer solution and the water drainage was recorded at 10 seconds after the treated wastewater is poured through the fabric filter. The filtrate samples were collected and were analyzed for PTSA concentration by fluorescence technique. FIG. 28 shows a plot of water drainage, % adsorption and tracer concentration in the filtrate against polymer dose in milliliters (ml) of one percent solution. The results showed that as polymer dose is increased from 2 milliliters to 4 milliliters, the water drainage increased from about 20 ml to 110 ml. Further increase in the polymer dose decreased the water drainage. Therefore the optimum polymer dose was 4 ml of polymer solution.

The filtrate tracer concentration shown on FIG. 28 did not show any trend with water drainage. This may be due to poor or no interaction between the polymer and Anthracenesulfonic acid.

TABLE I

Table I is a summary of tracers and sludges evaluated.

| Tracer | Type of Sludge | Mode of Addition | Excitation/Emission Wavelengths, nm | Polymer* | Performance** |
| --- | --- | --- | --- | --- | --- |
| Pyrenetetra sulfonic acid | Paper Mill A | To Sludge | 365/400 | DMAEM.MCQ/ Acrylamide 20 mole % | Excellent |
|  | Paper Mill A | To polymer |  | DMAEM.MCQ/ Acrylamide 20 mole % | Poor |
|  | Paper Mill B | To Sludge |  | DMAEM.MCQ/ Acrylamide 20 mole % | Excellent |
|  | Paper Mill B | To Polymer |  | DMAEM.MCQ/ Acrylamide 20 mole % | Excellent |
|  | Paper Mill C | To Sludge |  | DMAEM.MCQ/ Acrylamide 34 Mole % | Excellent |
|  | Textile Mill D | To Polymer |  | DMAEM.MCQ/ Acrylamide 50 Mole % | Excellent |
|  | Municipal Plant E | To sludge |  | DMAEA.MCQ/ Acrylamide 50 Mole % | Excellent |
| Triazole-Stilbene | Municipal Plant E | To Polymer | 363/451 | DMAEA.MCQ/ Acrylamide 50 M % | Excellent |
| Distyryl Biphenyl Derivative | Municipal Plant E | To Polymer | 354/427 | DMAEA.MCQ/ Acrylamide 50 Mole % | Excellent |
| Pyrenesulfonic Acid | Paper Mill A | To sludge | 342/376 | DMAEM.MCQ/ Acrylamide 20 mole % | Poor |
|  | Paper Mill A | to Polymer |  | DMAEM.MCQ/ Acrylamide 20 mole % | Poor |
| 8-Hydroxy 1,3,6 Pyrenetrisulfonic | Paper Mill A | To Sludge | 454/513 | DMAEM.MCQ/ Acrylamide 20 mole % | Excellent |
|  | Paper Mill A | To Polymer |  | DMAEM.MCQ/ Acrylamide 20 mole % | Poor |
| Anthracene Sulfonic Acid | Municipal Plant E | To Polymer | 258/416 | DMAEA.MCQ/ Acrylamide 50 Mole % | Poor |

*DMAEA.MCQ = Dimethylaminoethylacrylate methyl chloride quat
DMAEM.MCQ = Dimethylaminoethylmethacrylate methyl chloride quat
**Excellent = Filtrate tracer concentration correlated well with the sludge drainage
Poor = Filtrate tracer concentration did not show any trend with the sludge drainage

EXAMPLES OF FLUORESCENT TRACERS AND POLYMERS USED IN COLOR REMOVAL

Wastewater

The wastewater used in all the testing for color removal was from a Florida paper mill. The wastewater is a combination of washwater from the hard wood and soft wood pulp bleach plants, the recovery boiler, the digester and can contain some amount of lime. The pH of the wastewater varies from 7.0 to 11.5. The contribution to the color in the wastewater comes mainly from organic compounds such as lignin.

TESTING PROCEDURE

Color Removal Testing

A 10% solution of the polymer containing 200 ppm of the fluorescent tracer was added to 250 ml of the wastewater at different concentrations. The wastewater was mixed at 330 rpm for 1 minute and then mixed at 80 rpm for 5 minutes using a Phipps and Bird gang stirrer. The precipitated particles were then allowed to settle for 10 minutes, after which the supernatant was collected. The apparent color of the supernatant was determined by measuring the absorbance at 465 nm using a Hach DR-2000 unit. Some of the supernatant was filtered through a 0.8 mm filter and used for fluorescence analysis of the tracer. The pH of the rest of the supernatant was adjusted to 7.6 and then filtered through 0.8 mm filter for measurement of true color by absorbance at 465 nm.

Fluorescence Analysis

The supernatant (without pH adjustment) filtered through 0.8 mm filter was analyzed for the tracer concentration using a Gilford Fluoro IV fluorometer. The analysis was conducted in 10 mm path length quartz cuvettes at the appropriate excitation and emission wavelengths of the tracer. The instrument was calibrated with 0.1 ppm of the probe to be analyzed. Depending on the quenching of the fluorescent probe by the polymer, 4% $H_2SO_4$ or NaOH was used to negate the quenching effect, The same testing procedure was used for all the polymers and fluorescent probes.

Two different polymers were used for color removal:
1. Polymer F (Epi-DMA)—a copolymer of epichlorohydrin and dimethyl amine with a molecular weight of 20,000, intrinsic viscosity between 0.08 and 0.14 and an actives content of 50%.
2. Polymer G (PolyDADMAC)—a homopolymer of DADMAC (diallyldimethylammonium chloride) with a molecular weight of 150,000, intrinsic viscosity between 0.9 and 1.2 and an actives content of 15%.

EXAMPLE 6

Color removal

Figure 29:
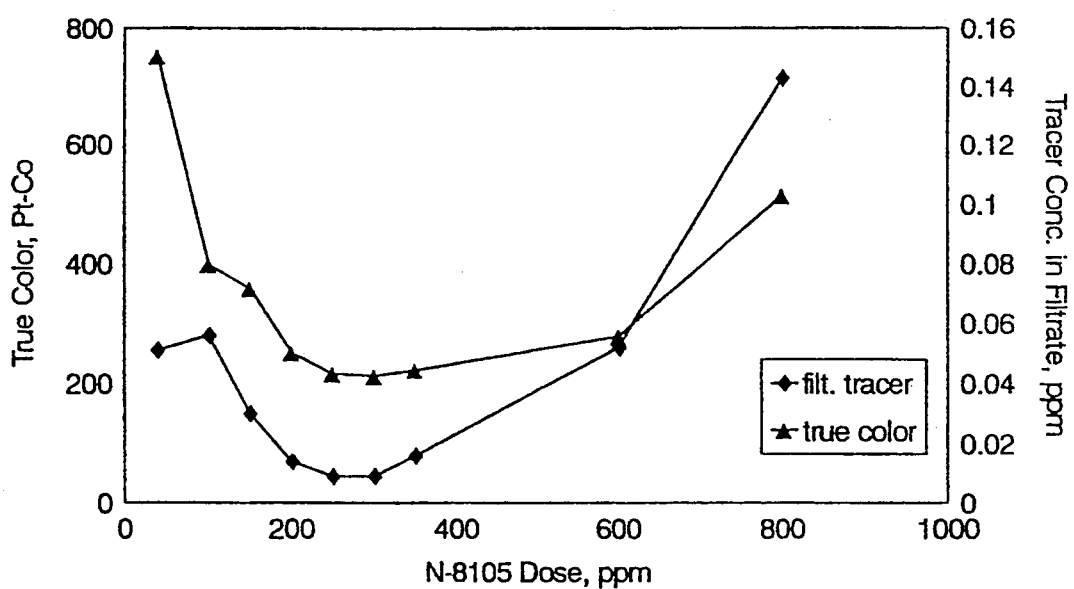
FIG. 29 is a graph comparing polymer dose to drainage and percentage adsorption for polymer F.

In this test, the epi-DMA polymer was used with 8-hydroxy 1,3,6 pyrenetrisulfonic acid as the fluorescent tracer. The plot of true color and tracer concentration as a function of the polymer dose is shown in FIG. 29. The true color initially decreases and then increases with increasing polymer dosage. The polymer dose corresponding to the minimum color is the optimum dose. The tracer concentration shows a similar profile and the minimum tracer concentration thus corresponds to the optimum dose.

EXAMPLE 7

Color removal

Figure 30:
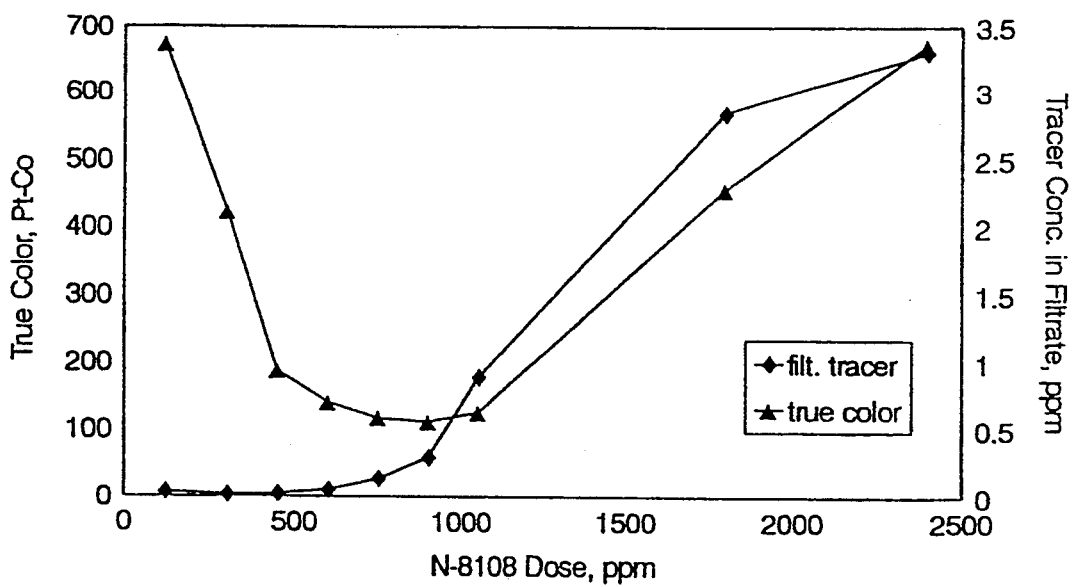
FIG. 30 is a graph comparing polymer dose to drainage and percentage adsorption for polymer G.

In this test, the polyDADMAC was used with 1,3,6,8 pyrenetetrasulfonic acid as the probe. The plot of true color and tracer concentration as a function of the polymer dose is shown in FIG. 30. The true color initially decreases and then increases with increasing polymer dosage. The polymer dose corresponding to the minimum color is the optimum dose. The tracer concentration is initially constant and then shows a sudden increase with increasing polymer dose. The polymer dose at which this sudden change occurs is when the minimum in true color is obtained.

The following tracers were used with epi-DMA polymer (TABLE II).

| Probe | Excit. wavelength | Emiss. wavelength | Effectiveness |
| --- | --- | --- | --- |
| 1,3,6,8 pyrenetetrasulfonic acid (PTSA) | 365 | 400 | + |
| 1 pyrenesulfonic acid | 342 | 376 | − |
| 8-hydroxy 1,3,6 pyrenetrisulfonic acid | 454 | 513 | + |
| naphthalenesulfonic acid | 277 | 334 | + |
| 1,5 naphthalenedisulfonic acid | 295 | 330 | + |
| 1,3,6 naphthalenetrisulfonic acid | 288 | 341 | + |
| resazurin | 568 | 579 | + |
| tinopal CBS-X | 354 | 427 | − |
| tolytriazole | 280 | 410 | + (pH 9–12) |

1 pyrenesulfonic acid did not show any correlation due to severe quenching of the probe's fluorescence by the polymer Acid or alkali addition did not negate the quenching effect.

Tinopal CBS-X did not show any correlation due to the very low solubility of the probe in water.

The polyDADMAC polymer was tested only with 1,3,6,8 pyrenetetrasulfonic acid.

Examples of Use of Fluorescent Tracer in Oily Wastewater Clarification

EXAMPLE 8

Oil-in-water Emulsion Breaking

Figure 31:
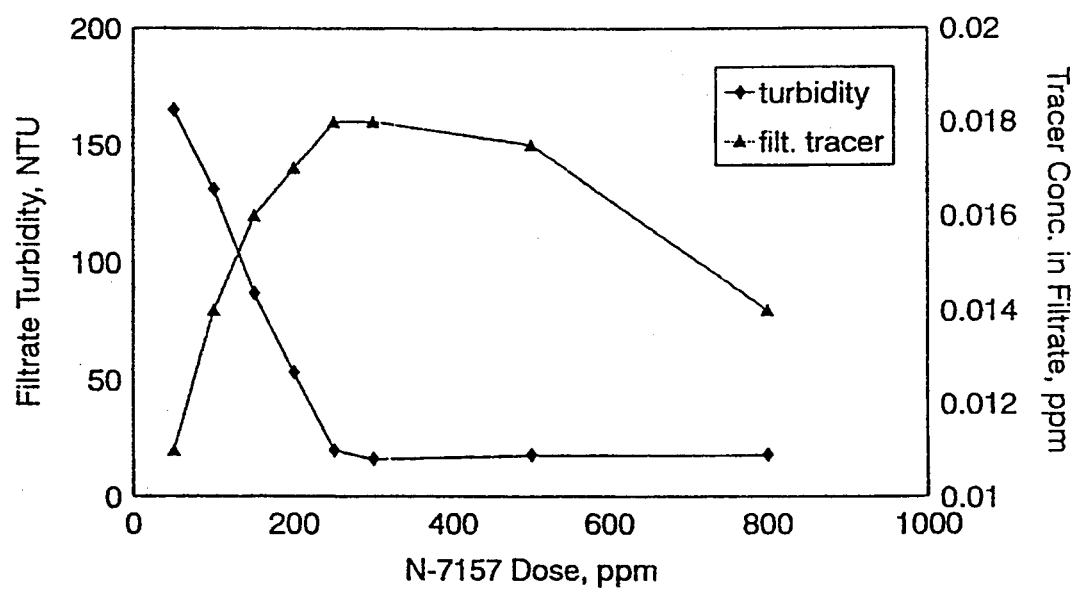
FIG. 31 is a graph comparing polymer dose to drainage and percentage adsorption for polymer F.

The test was conducted on a wastewater from an Alabama paper mill. The wastewater was an oil-in-water emulsion. The fluorescent tracer used in this test was 1,3,6,8 pyrenetetrasulfonic acid and the polymer used was N-7157. N-7157 is a blend of polyaluminum chloride and epi-DMA (epi-DMA is a copolymer of epichlorohydrin and dimethyl amine). A 10% solution of the polymer containing 100 ppm of the tracer was added at different concentrations to the wastewater. The wastewater was stirred at 100 rpm for 5 minutes and then mixed at 30 rpm for 2 minutes on a Phipps and Bird gang stirrer. The precipitated oil was allowed to settle for 5 minutes, after which the supernatant was collected. The supernatant turbidity was measured using a Hach turbidimeter. The supernatant was also measured for the concentration of the tracer using a Gilford Fluoro IV fluorometer. The results are shown in FIG. 31. The turbidity of the supernatant initially decreases with increasing polymer dose and then remains fairly constant. The dose at which the turbidity attains a constant value is the optimum dose. The tracer concentration initially increases with the polymer dose and then decreases. The maximum in tracer concentration corresponds to the optimum polymer dose.

EXAMPLE 9

Oil-in-water Emulsion Breaking

Figure 32:
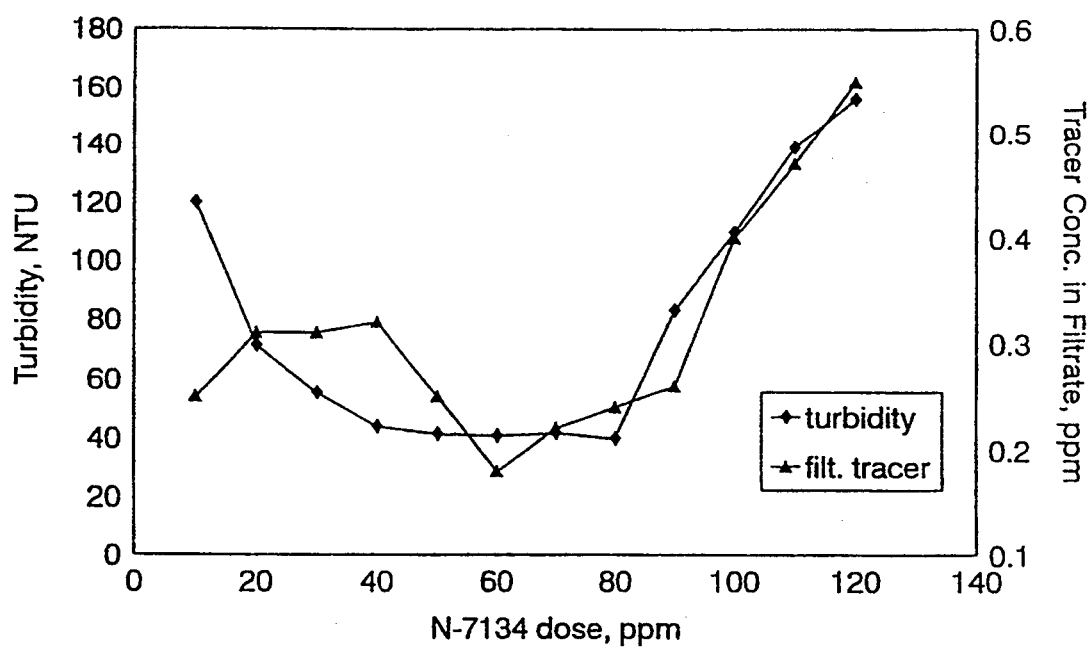
FIG. 32 is a graph comparing polymer dose to drainage and percentage adsorption for polymer G.

The test was conducted on a wastewater from an Illinois refinery. The wastewater was an oil-in-water emulsion. The fluorescent tracer used was 1,3,6,8, pyrenetetrasulfonic acid and the polymer used was Polymer D, a copolymer of ethylenedichloride and ammonia. The polymer has a molecular weight of 60,000, intrinsic viscosity of 0.33 and an actives content of 19%. A 10% solution of the polymer containing 2000 ppm of the tracer was added at different concentrations to the wastewater. The wastewater was stirred at 100 rpm for 5 minutes and then mixed at 30 rpm for 2 minutes on a Phipps and Bird gang stirrer. The precipitated oil was allowed to settle for 5 minutes, after which the supernatant was collected. The supernatant turbidity was measured using a Hach turbidimeter. The supernatant was also measured for the concentration of the tracer using a Gilford Fluoro IV fluorometer. The results are shown in FIG. 32. The turbidity of the supernatant initially decreased with increasing polymer dose and then increased with overdose of the polymer. The tracer concentration shows a similar profile with polymer dose and the minimum in tracer concentration reflects the optimum polymer dose.

Changes can be made in the composition, operation and arrangement of the method of the present invention described herein without departing from the concept and scope of the invention as defined in the following claims:

We claim:

1. A method for optimizing the dosage of a polyelectrolyte treating agent in a water treatment process, the water treatment process being conducted to produce an aqueous effluent substantially free of contaminants, the method comprising the steps of:

adding an effective amount of a polyelectrolyte treating agent to water including contaminants to remove said contaminants in said water treatment process;

adding to the water from about 0.001 to about 750,000 parts per million based on the amount of the added polyelectrolyte which is being added to the process of a fluorescent material having an opposite electrical charge as the polyelectrolyte;

forming a complex between the fluorescent material and the polyelectrolyte, which complex does not impede activity or charge neutralization ability of the polyelectrolyte;

conducting the water treatment process to obtain the aqueous effluent, which effluent includes the complex;

detecting the amount of fluorescent material in the aqueous effluent; and adjusting the amount of the polyelectrolyte added to the water based upon the detected amount of fluorescent material in the aqueous effluent.

2. The method of claim 1 wherein the water treatment process is selected from the group consisting of raw water clarification, sludge dewatering, emulsion breaking, and color removal.

3. The method of claim 1 wherein the fluorescent material is anionic and the polyelectrolyte is cationic.

4. The method of claim 3 wherein the anionic fluorescent material is added to the water at a level of from about 0.01 to about 200,000 parts per million based on the weight of the cationic polyelectrolyte.

5. The method of claim 3 wherein the step of detecting is carried out continuously by the use of a fluorometer, and the amount of cationic polyelectrolyte is adjusted continuously.

6. A method for adjusting the optimum dosage of a water soluble synthetic cationic polyelectrolyte being utilized in a color removal process in which the cationic polyelectrolyte is being added in an effective amount to neutralize the electrostatic charge of colored impurities suspended in a wastewater so as to improve the separation of colored bodies from the water and to produce an aqueous effluent containing less colored impurities, the method comprising the steps of:

adding to the waterwaste from about 0.001 to about 750,000 parts per million based on the amount of the cationic polyelectrolyte being added to the process of a water soluble anionically charged fluorescent material;

forming a complex between the fluorescent material and the polyelectrolyte, which complex does not impede activity or charge neutralization ability of the polyelectrolyte conducting the color removal process to obtain the aqueous effluent, which effluent includes the complex;

measuring the amount of anionically charged fluorescent material in the aqueous effluent; and adjusting the amount of the cationic polyelectrolyte added to the wastewater based upon the measured amount of anionically charged fluorescent material in the aqueous effluent.

* * * * *